United States Patent
Cole et al.

(10) Patent No.: US 10,696,976 B2
(45) Date of Patent: Jun. 30, 2020

(54) SOYBEAN PLANT AND SEED CORRESPONDING TO TRANSGENIC EVENT MON87712 AND METHODS FOR DETECTION THEREOF

(71) Applicant: Monsanto Technology LLC, St. Louis, MO (US)

(72) Inventors: Robert H. Cole, Florissant, MO (US); John A. Korte, Westerly, RI (US); John R. LeDeaux, St. Louis, MO (US); Melissa Compton Spears, St. Louis, MO (US); Kunsheng Wu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/033,088

(22) Filed: Jul. 11, 2018

(65) Prior Publication Data
US 2019/0002907 A1    Jan. 3, 2019

Related U.S. Application Data

(62) Division of application No. 15/343,049, filed on Nov. 3, 2016, now Pat. No. 10,053,704, which is a division of application No. 13/879,238, filed as application No. PCT/US2011/055799 on Oct. 11, 2011, now Pat. No. 9,493,786.

(60) Provisional application No. 61/392,267, filed on Oct. 12, 2010, provisional application No. 61/393,448, filed on Oct. 15, 2010.

(51) Int. Cl.
C12N 15/82 (2006.01)
C12Q 1/68 (2018.01)
A01H 5/10 (2018.01)
C12Q 1/6895 (2018.01)
A01H 1/02 (2006.01)

(52) U.S. Cl.
CPC .......... *C12N 15/8261* (2013.01); *A01H 1/02* (2013.01); *A01H 5/10* (2013.01); *C12Q 1/6895* (2013.01); *C12Q 2600/13* (2013.01); *C12Q 2600/156* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,067,627 B2 | 6/2006 | Cohen et al. | |
| 7,692,067 B2 | 4/2010 | Creelman et al. | |
| 7,960,607 B2 | 6/2011 | Molinero | |
| 8,088,976 B2 | 1/2012 | Boukharov et al. | |
| 2004/0078852 A1 | 4/2004 | Thomashow et al. | |
| 2007/0128225 A1 | 6/2007 | Prior et al. | |
| 2009/0282497 A1* | 11/2009 | Beazley | A01H 5/00 800/260 |
| 2014/0380520 A1 | 12/2014 | Khanna et al. | |
| 2019/0002908 A1 | 1/2019 | Cole et al. | |

FOREIGN PATENT DOCUMENTS

| | | |
|---|---|---|
| WO | WO 2008/005210 | 1/2008 |
| WO | WO 2009/055597 | 4/2009 |
| WO | WO 2009/064652 | 5/2009 |
| WO | WO 2009/102873 | 8/2009 |

OTHER PUBLICATIONS

U.S. Appl. No. 15/802,397, filed Nov. 2, 2017, Khanna et al.
Anklam et al., "Analytical methods for detection and determination of genetically modified organisms in agricultural crops and plant-derived food products", *Eur. Food Res. Technol.*, 214:3-26, 2011.
Axelos et al., "The gene family encoding the *Arabidopsis thaliana* translation elongation factor EF-1 alpha: molecular cloning, characterization and expression," *Mol. Gen. Genet.*, 219:106-112, 1989.
Barker et al., "Nucleotide sequence of the T-DNA region from the *Agrobacterium tumefaciens* octopine Ti plasmid pTi15955," *Plant Mol. Biol.*, 2:335-350, 1983.
Coruzzi et al., "Tissue-specific and light-regulated expression of a pea nuclear gene encoding the small subunit of ribulose-1,5-bisphosphate carboxylase," EMBO J., 3:1671-1679, 1984.
Depicker et al., "Nopaline synthase: transcript mapping and DNA sequence," *J. Mol. Appl. Genet.*, 1:561-573, 1982.
Fling et al., "Nucleotide sequence of the transposon Tn7 gene encoding an aminoglycoside-modifying enzyme, 3"(9)-O-nucleotidyltransferase," *Nucl. Acids Res.*, 13(19):7095-7106, 1985.
Giza et al., "A self-inducing runaway-replication plasmid expression system utilizing the Rop protein," *Gene*, 78:73-84, 1989.
Holtan et al., "BBX32, an *Arabidopsis* B-Box protein, functions in light signaling by suppressing HY5-regulated gene expression and interacting with STH2/BBX21," *Plant Physiol.*, 156(4):2109-2123, 2011.
John, "Structural characterization of genes corresponding to cotton fiber mRNA, E6: reduced E6 protein in transgenic plants by antisense gene," *Plant Mol. Biol.*, 30:297-306, 1996.

(Continued)

*Primary Examiner* — Bratislav Stankovic
(74) *Attorney, Agent, or Firm* — Dentons US LLP; David Lanzotti, Esq.

(57) ABSTRACT

The present invention provides a transgenic soybean comprising event MON87712 that exhibits increased yield. The invention also provides cells, plant parts, seeds, plants, commodity products related to the event, and DNA molecules that are unique to the event and were created by the insertion of transgenic DNA into the genome of a soybean plant. The invention further provides methods for detecting the presence of said soybean event nucleotide sequences in a sample, probes and primers for use in detecting nucleotide sequences that are diagnostic for the presence of said soybean event.

6 Claims, 2 Drawing Sheets
Specification includes a Sequence Listing.

(56) References Cited

OTHER PUBLICATIONS

Kay et al., "Duplication of CaMV 35S promoter sequences creates a strong enhancer for plant genes," *Science*, 236:1299-1302, 1987.
Khanna et al., "The *Arabidopsis* B-Box Zinc Finger Family," *Plant Cell*, 21:3416-3420, 2009.
Koyejo et al., "Petition for the Determination of Nonregulated Status for MON 87712 Soybean", Jul. 19, 2011.
Klee et al., "Cloning of an *Arabidopsis thaliana* gene encoding 5-enolpyruvylshikimate-3-phosphate synthase: sequence analysis and manipulation to obtain glyphosate-tolerant plants," *Molec. Gen. Genet.*, 210:437-442, 1987.
LW et al., "An Accurate and Rapid PCR-Based Zygosity Testing Method for Genetically Modified Maize," GMO *Biosafety Research*, 1(1):1-4, 2010.
Odell et al., "Identification of DNA sequences required for activity of the cauliflower mosaic virus 35S promoter," *Nature*, 313:810-812, 1985.
Padgette et al., "New Weed Control Opportunities: Development of Soybeans with a Roundup Ready™ Gene," in *Herbicide-Resistant Crops* Ch. 4, pp. 53-84, CRC Press, 1996.
Richins et al., "Sequence of figwort mosaic virus DNA (caulimovirus group)," *Nucl. Acids Res.*, 15:8451-8466, 1987.
Stalker et al., "Nucleotide sequence of the region of the origin of replication of the broad host range plasmid RK2," *Molec. Gen. Genet.*, 181:8-12, 1981.
Sutcliffe, "Complete nucleotide sequence of the *Escherichia coli* plasmid pBR322," Cold *Spring Harbor Symposia on Quantitative Biology* 43:77-90, Cold Spring Harbor Laboratory Press, 1979.
Zambryski et al., "Tumor induction by *Agrobacterium tumefaciens*: analysis of the boundaries of T-DNA," *J Mol. Appl. Genet.*, 1:361-370, 1982.
*Arabidopsis thaliana* At3g21150 mRNA, complete cds, GenBank, published Mar. 14, 2003.
Office Action regarding Indonesian Application No. W00201302014, dated Jun. 27, 2016.
U.S. Appl. No. 16/033,091, filed Jul. 11, 2018, Cole et al.
USPTO: Notice of Allowance regarding U.S. Appl. No. 16/033,091, dated Jan. 13, 2020.

\* cited by examiner

SEQUENCE LISTING

```
<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: 5' junction

<400> SEQUENCE: 1
ctataagtat ttgatggtca at                                              22

<210> SEQ ID NO 2
<211> LENGTH: 22
<212> TYPE: DNA
<213> ORGANISM: Artificial sequence
<220> FEATURE:
<223> OTHER INFORMATION: 3' junction

<400> SEQUENCE: 2
tcagtgtttg atttacttaa ac                                              22

<210> SEQ ID NO 3
<211> LENGTH: 3605
<212> TYPE: DNA
<213> ORGANISM: Artificial sequence
<220> FEATURE:
<223> OTHER INFORMATION: 5' flank + 100 bp insert
<220> FEATURE:
<221> NAME/KEY: misc_feature
<222> LOCATION: (3451)..(3463)
<223> OTHER INFORMATION: The sequence at position 3451 to 3463 may
      contain additional c residues including, for example, from 13 to
      100 or more total consecutive c residues.

<400> SEQUENCE: 3
```

```
gtcgtcgaag gtgtgtcgtt gaagctcctt tttttaagta gtggtagaaa tactagaaat    60
ataatatgca tgggataatc attaacttac cttaaagagt tggaagaagg catccttttc   120
atggtctttc attgctccgt atgtaggcca tggatgaaga aactattgct tgatggtcgt   180
tgagatagct tgtgacgcaa tcctgcttgg ttcaaaccta aatacaaaag aagggtacac   240
aaaattaaaa gacaatgaat gagttataat atatattgaa aaagttttga attctaattt   300
actcttaccc tccacccctg ggtataatca tagggcgatc attgggtaag ggttctttca   360
tttccccgtc taaatcatgt tcattgatag acaatttata taatgatata ttatattaat   420
acatatttaa attttcactt ttaaatatat ctaaaaaatc ttttaatcaa taataagtat   480
aacaatttaa tatatatata tatcattata tttaacaacg ttaaccatta aaatttcctt   540
atgtgtttaa ctatttaatg agtcatttt tattatctca cgtgtttaat aacattcaat    600
gggtcttgtt tcttttttg accgattttg tttattatcg atgaattata ttaccgacaa    660
aacatttgtc ggaaagctct gtcgataatg ctaacttttc tgacaaatat ttatccatcg   720
aaaaagttcc atcacaaata aataatttaa aaattcatca gaaaaaattc atatttccta   780
catactataa tccgtcagaa atttccattg gaactaacaa catttttatg gacatatatt   840
cgtcggaaca ctctatcgtt aattttaatg tttatgataa atttagatct gtcaattata   900
tttcgccgaa aatcgacgct tttttgtag tgattaattc aatgatgaaa tgaattatat    960
taatgatgat atatgaatgt attaatgatg agatatgaca ttgtttgaaa tgattataat  1020
atacatgcat ctatgaatga cattgcatat gagttggcac gtaagttgag actacttaga  1080
aggccctcaa cctagtgttg gaggttgaca tggtggctat agaatgaata ggtgggtgaa  1140
tccttgtata ggttaaggtg tttgcaagcc ttatcgaggc aagccattat ccatactcat  1200
caatttttaga tacaaccaca cttccttcat agggttaatt ggagtctccc tgagtggtca  1260
aggtgtgact atgttaaggg atgtactagg ttaatcgctc aaaaagtaaa atctccttgg  1320
agtaaagtgt caacatgtca tatcataata catagacatg tgcatttacc tttatgaata  1380
aagaagaatg acatgttact atatgagtta tggaaatgct ttgatgtatg atgattgaat  1440
ctttatgtaa tgcttgatga actaacgatt ataagattga ccttaaaaca acaaagatta  1500
ataacaattg ctataaaaca aacttgtatt ttatcttcgt tacctttctt aataatgaaa  1560
aataatttga aaaaagcgag tatggccata aggcacatag ttttcaatt gtatatacat   1620
atcatatgat gtcttcttat cttatcatgt gttttggctt tttagcttgg aaagcgtgaa  1680
aaatttataa gtattttcac aattaaatta atagaagggt tttaaaagaa ttaaaataaa  1740
gtcttccgct tgagtagttc ttagtggtat ataaccatga caaatcatta caattacaag  1800
taagaaagac atatttaagg caaaaaatag tcttcgacta tcggttaagg acattattag  1860
tgcattcaaa aagaaaaaa aacaaaaaca aatttttttt attgtagcca actagaatat  1920
aaagatgttg aagcaggtta ttgtacaaaa gttaattatt ggcaaatatg acaggtattt  1980
tgtatttttt attttgccat aacattgata caaaatattt acatacttta ttgatgacta  2040
atatttttta agaaacctaa ctaaactatc tataataaag tctctcattt taattacatt  2100
tttgttttca ttgatgagac ttgaaccaaa acctttgtca agggatcaaa cacaattctc  2160
cacacaaacc aataaatcaa catgtttgtt taaagttgag attagagata ctaattcata  2220
cttataacat agcataaaat atttatatta tttgaaaaat aaaataagtc agaaagaaat  2280
aatataagat tcttttgttt aattaaatga ttagaaagaa aaataaatag tataaaataa  2340
```

```
ttttaggtta attatttatt ttaactctat agttatctcc tttttaagat ttagttttgt      2400
acgaaaaaaa tataaattgt aattcttata tatacataaa agttaaattt taccaaaagc      2460
attaaacttt ttaatctatt attattttc taacatgaaa ctattaaata ttaattttaa      2520
ttttttatgt tataaagaaa tttatttaac ttttaagaa taaaaattaa aaaatgaaaa      2580
gagattttat tctctttatt tatgccacag gcagggacag aggcagaaat aaacattagg      2640
gggccaattt tgaaattaaa atttatctaa ttaaaaaatg tatgagtatt aattttaaac      2700
aaactactgc taatatgttt tttccaaaaa aaattcaatg acatataata gaaatatatt      2760
cacataaaag acaaattaaa catttaaaaa atctattaca aatgtcattt gacatgctac      2820
catgatttag tttctaatat ttactttgtt tttccaaaat ctagtcaata gtgtgcctag      2880
accatgcact caatgttaaa agcatgtagg agcatcacaa tgacaataaa atcaagataa      2940
tattttatat aatgttcata attaagcttg tcccatagac aaagattact aaataatttt      3000
aacttctcaa ataattata atcaaatcaa tataaaggaa gaataataat gtcttttaat      3060
cacaaatgca ataatttata accttttaaaa tagtataaaa aattataaaaa ataaaattta      3120 tgaaaaaaat aaatgagact taaattttt taaaaagaca aaatgtaaaa ttttttacaat      3180 aaaatctact aaaaagaaat agaataattg tttttaaaaaaa aataaaaatg tcattatagt      3240
tatgcaaaac tataaaggat aattgattat tttattaaaa aaataaaaat aacattttaa      3300
tataattatt tttataatta aacttttaaaa aaataattat ctaaattta aaatattatg      3360 tatattaaaa aataaaacta aaaaaaaag ttagggggggc ctcgcacctc cgtatctggc      3420
cgcaggagaa gttatcacat gagttcgcg ccccccccc cccgccgccc ctattttt      3480 ttttctatta tttgctataa gtatttgatg gtcaatatgg agaaaagaa agagtaatta      3540 ccaattttt ttcaattcaa aaatgtagat gtccgcagcg ttattataaa atgaaagtac      3600
atttt                                                                3605
```

<210> SEQ ID NO 4
<211> LENGTH: 2065
<212> TYPE: DNA
<213> ORGANISM: Artificial sequence
<220> FEATURE:
<223> OTHER INFORMATION: 3' flank + 100 bp insert

<400> SEQUENCE: 4

```
ataaaaatgt gagtacattc tcgagcagga cctgcagaag ctagcttgat ggggatcaga      60
ttgtcgtttc ccgccttcag tttaaactat cagtgtttga tttacttaaa cgaggtaatt     120
gtaaaactta aacttgatat agttaaatgt tatatatata tatatataat acttaactta     180
tttaattatc aaaatttatt ttgaaccaaa cttttactaa tttaatatta atttattttt     240
ttgttaaaaa ggcaagtaaa gtaataaaaa aattcataaa atgatttaaa attatagagt     300
gataaactta tctttttag tacataaaat ttcaaaaacg gagaccatga tgtctttagg     360
attaaaaagt aattaaagga aaaatgtaaa aaaaaaaag ttaaggaact aaaaataagg     420 ataaaagtt aaagaatgtt gatcaataaa aaaagagt tcaataacta aaaacaaaaa     480
tcctaaaaat attagtgact agtaaatact aatcttgaac aacgttctat caataattca     540
attaaagatc gagtgaagga agaatgcttc tttaaaaata aactaataaa gagatatata     600
catttcatac ttttttttat cacgtataca tttctctctt aaaaaaccat atatacattt     660
ctaaagaaaa tattgcacat ttctactttc aaaatacatt tgacggtaac atgtagatgg     720
agggaaaaat tatggtttt catttttatt ttagtgttaa tttatttta ttattatttt     780
```

```
ttttatctta tttgatagcc tgacattttt ttgatttgtt tttttattaa ttgtgtgtaa      840
agacaaagta ttagatttgt gcaaataaac taggtcaaga ctaaagttta tttaatttta      900
aagactagac tttagatcat ttaaaaaaaa ttttaagtct aacatgtcaa cctatttaag      960
taaatgtaag tatttaattt ttgttgttat tttttataat ggataggtat tcagttggtt     1020 caagaaccc ataaccatcc ctactaaata ggtatccagt cttaccccca attggccccc      1080
acaaacaggt gattaaaccc ataataaaaa aagtgaattg attaagggaa aagagaagtt     1140
taggccactt aaaccccaat tatggaagaa ttacctagac ggtaatccaa gcacaaaggt     1200
ccatggttca aggcccacaa atgtttgtat aaatagggg aaaaccctaa gtaatgacca      1260
ttgttcgttt gatgtgcatt ttattgcctt gcttactact cacaattgaa ctctgactta     1320
agcgtttgag tatcttttgc aagtatcccc cccttgggtc atcttatttg gcacgtgaag     1380
aagacaaagt ccaaaggcag gaccttcta ttagagggac agtgtccgac cattatttgg      1440
taggaatatt ttggcacccc aaagtaagat agtccttgac cctaagaatt atggcaatca     1500
cacgcacaag aaccaacata gcagcaaaaa ccaacttggg aatcattagc ctgaagaagt     1560
ccatgtagag ggctagattg acttatcctt aatggtgagg aggctacaag cacaagtatt     1620
agatatgcgt caacatcatg tcgaagaggt cattacccctt tgacaagaaa atgcacaact     1680
acaagagggt aaccgttcct agaaacccga aaatgaaaca cctgttggag cggaggtaga     1740
gtcaaccaat tttgagatgc caaaagccac caatgttagt gtttggcagg atacacaccc     1800
tcagttcata aatatgttag ggaagcaact acagtagttc aagaacacct ttttcctcgg     1860
tgtcatggaa gccacccctcc ttcccaacta gaagaacctc accatcgaga agtactatgg     1920
taccactaac ccatatgagc accttgacgt ttatatcacc caagtcagcc tgtacactat     1980
ggataatgtt gtcttatgcc aggtgttccc tacatctttg aaggggtaga tcctccatta     2040
gttcacccac ctccctcccc caaca                                          2065
```

<210> SEQ ID NO 5
<211> LENGTH: 2014
<212> TYPE: DNA
<213> ORGANISM: Artificial sequence
<220> FEATURE:
<223> OTHER INFORMATION: insert

<400> SEQUENCE: 5

```
tgatggtcaa tatggagaaa aagaaagagt aattaccaat tttttttcaa ttcaaaaatg        60
tagatgtccg cagcgttatt ataaaatgaa agtacatttt gataaaacga caaattacga       120
tccgtcgtat ttataggcga aagcaataaa caaattattc taattcggaa atctttattt       180
cgacgtgtct acattcacgt ccaaatgggg gcttagatga gaaacttcac gatttggcgc       240
gccaaagctt gatatcgaat tcctgcagcc cccttaaagg gggggatccg gtccgatgtg       300
agacttttca acaagggta atatccggaa acctcctcgg attccattgc ccagctatct       360
gtcactttat tgtgaagata gtggaaaagg aaggtggctc ctacaaatgc catcattgcg       420
ataaaggaaa ggccatcgtt gaagatgcct ctgccgacag tggtcccaaa gatggacccc       480
cacccacgag gagcatcgtg gaaaagaag acgttccaac cacgtcttca aagcaagtgg       540
attgatgtga tggtccgatt gagactttttc aacaagggt aatatccgga acctcctcg       600 gattccattg cccagctatc tgtcactttta ttgtgaagat agtggaaaag gaaggtggct      660
cctacaaatg ccatcattgc gataaaggaa aggccatcgt tgaagatgcc tctgccgaca      720
```

| | |
|---|---|
| gtggtcccaa agatggaccc ccacccacga ggagcatcgt ggaaaaagaa gacgttccaa | 780 |
| ccacgtcttc aaagcaagtg gattgatgtg atatctccac tgacgtaagg gatgacgcac | 840 |
| aatcccacta tccttcgcaa gacccttcct ctatataagg aagttcattt catttggaga | 900 |
| ggaccaggtg gtaccggcgc gccaccatgg tgagcttttg cgagctttgt ggtgccgaag | 960 |
| ctgatctcca ttgtgccgcg gactctgcct tcctctgccg ttcttgtgac gctaagttcc | 1020 |
| atgcctcaaa ttttctcttc gctcgtcatt tccggcgtgt catctgccca aattgcaaat | 1080 |
| ctcttactca aaatttcgtt tctggtcctc ttcttccttg gcctccacga acaacatgtt | 1140 |
| gttcagaatc gtcgtcttct tcttgctgct cgtctcttga ctgtgtctca agctccgagc | 1200 |
| tatcgtcaac gacgcgtgac gtaaacagag cgcgagggag ggaaaacaga gtgaatgcca | 1260 |
| aggccgttgc ggttacggtg gcggatggca tttttgtaaa ttggtgtggt aagttaggac | 1320 |
| taaacaggga tttaacaaac gctgtcgttt catatgcgtc tttggctttg gctgtggaga | 1380 |
| cgaggccaag agcgacgaag agagtgttct tagcggcggc gttttggttc ggcgttaaga | 1440 |
| acacgacgac gtggcagaat ttaaagaaag tagaagatgt gactggagtt tcagctggga | 1500 |
| tgattcgagc ggttgaaagc aaattggcgc gtgcaatgac gcagcagctt agacggtggc | 1560 |
| gcgtggattc ggaggaagga tgggctgaaa acgacaacgt ttaggcgatc gcgggccctg | 1620 |
| atcacctgtc gtacagtatt tctacatttg atgtgtgatt tgtgaagaac atcaaacaaa | 1680 |
| acaagcactg gctttaatat gatgataagt attatggtaa ttaattaatt ggcaaaaaca | 1740 |
| acaatgaagc taaaatttta tttattgagc cttgcggtta atttcttgtg atgatctttt | 1800 |
| tttttatttt ctaattatat atagtttcct ttgctttgaa atgctaaagg tttgagagag | 1860 |
| ttatgctctt ttttcttcc tctttctttt ttaactttat catacaaatt ttgaataaaa | 1920 |
| atgtgagtac attctcgagc aggacctgca gaagctagct tgatggggat cagattgtcg | 1980 |
| tttcccgcct tcagtttaaa ctatcagtgt ttga | 2014 |

<210> SEQ ID NO 6
<211> LENGTH: 7484
<212> TYPE: DNA
<213> ORGANISM: Artificial sequence
<220> FEATURE:
<223> OTHER INFORMATION: flanks + insert
<220> FEATURE:
<221> NAME/KEY: misc_feature
<222> LOCATION: (3451)..(3463)
<223> OTHER INFORMATION: The sequence at position 3451 to 3463 may
    contain additional c residues including, for example, from 13 to
    100 or more total consecutive c residues.

<400> SEQUENCE: 6

| | |
|---|---|
| gtcgtcgaag gtgtgtcgtt gaagctcctt tttttaagta gtggtagaaa tactagaaat | 60 |
| ataatatgca tgggataatc attaacttac cttaaagagt tggaagaagg catccttttc | 120 |
| atggtctttc attgctccgt atgtaggcca tggatgaaga aactattgct tgatggtcgt | 180 |
| tgagatagct tgtgacgcaa tcctgcttgg ttcaaaccta aatacaaaag aagggtacac | 240 |
| aaaattaaaa gacaatgaat gagttataat atatattgaa aaagttttga attctaattt | 300 |
| actcttaccc tccaccccctg gtataatca tagggcgatc attgggtaag ggttctttca | 360 |
| tttccccgtc taaatcatgt tcattgatag acaatttata taatgatata ttatattaat | 420 |
| acatatttaa attttcactt ttaaatatat ctaaaaaatc ttttaatcaa taataagtat | 480 |
| aacaatttaa tatatatata tatcattata tttaacaacg ttaaccatta aaatttcctt | 540 |
| atgtgtttaa ctatttaatg agtcattttt tattatctca cgtgtttaat aacattcaat | 600 |

```
gggtcttgtt tcttttttg accgattttg tttattatcg atgaattata ttaccgacaa     660
aacatttgtc ggaaagctct gtcgataatg ctaacttttc tgacaaatat ttatccatcg     720
aaaaagttcc atcacaaata aataatttaa aaattcatca gaaaaaattc atatttccta     780
catactataa tccgtcagaa atttccattg aactaacaa cattttttatg acatatatt     840 cgtcggaaca ctctatcgtt aattttaatg tttatgataa atttagatct gtcaattata     900
tttcgccgaa aatcgacgct ttttttgtag tgattaattc aatgatgaaa tgaattatat     960
taatgatgat atatgaatgt attaatgatg agatatgaca ttgtttgaaa tgattataat    1020
atacatgcat ctatgaatga cattgcatat gagttggcac gtaagttgag actacttaga    1080
aggccctcaa cctagtgttg gaggttgaca tggtggctat agaatgaata ggtgggtgaa    1140
tccttgtata ggttaaggtg tttgcaagcc ttatcgaggc aagccattat ccatactcat    1200 caatttttaga tacaaccaca cttccttcat agggttaatt ggagtctccc tgagtggtca    1260
aggtgtgact atgttaaggg atgtactagg ttaatcgctc aaaagtaaa atctccttgg    1320 agtaaagtgt caacatgtca tatcataata catagacatg tgcatttacc tttatgaata    1380
aagaagaatg acatgttact atatgagtta tggaaatgct ttgatgtatg atgattgaat    1440
ctttatgtaa tgcttgatga actaacgatt ataagattga ccttaaaaca acaaagatta    1500
ataacaattg ctataaaaca aacttgtatt ttatcttcgt tacctttctt aataatgaaa    1560
aataatttga aaaaagcgag tatggccata aggcacatag tttttcaatt gtatatacat    1620
atcatatgat gtcttcttat cttatcatgt gttttggctt tttagcttgg aaagcgtgaa    1680
aaatttataa gtattttcac aattaaatta atagaagggt tttaaaagaa ttaaaataaa    1740
gtcttccgct tgagtagttc ttagtggtat ataaccatga caaatcatta caattacaag    1800
taagaaagac atatttaagg caaaaaatag tcttcgacta tcggttaagg acattattag    1860
tgcattcaaa aaagaaaaaa aacaaaaaca aaattttttt attgtagcca actagaaatat    1920 aaagatgttg aagcaggtta ttgtacaaaa gttaattatt ggcaaatatg acaggtattt    1980 tgtattttt atttgccat aacattgata caaaatattt acatacttta ttgatgacta    2040 atattttta agaaacctaa ctaaactatc tataataaag tctctcattt taattacatt    2100
tttgttttca ttgatgagac ttgaaccaaa accttttgtca agggatcaaa cacaattctc    2160
cacacaaacc aataaatcaa catgtttgtt taaagttgag attagagata ctaattcata    2220
cttataacat agcataaaat atttatatta tttgaaaaat aaaataagtc agaaagaaat    2280
aatataagat tcttttgttt aattaaatga ttagaaagaa aaataaatag tataaaataa    2340
ttttaggtta attatttatt ttaactctat agttatctcc tttttaagat ttagttttgt    2400
acgaaaaaaa tataaattgt aattcttata tatacataaa agttaaattt taccaaaagc    2460
attaaacttt ttaatctatt attatttttc taacatgaaa ctattaaata ttaatttttaa    2520 ttttttatgt tataaagaaa tttatttaac tttttaagaa taaaaattaa aaatgaaaa    2580 gagatttat tctctttatt tatgccacag gcagggacag aggcagaaat aaacattagg    2640
gggccaattt tgaaattaaa atttatctaa ttaaaaaatg tatgagtatt aattttaaac    2700
aaactactgc taatatgttt tttccaaaaa aaattcaatg acatataata gaaatatatt    2760
cacataaaag acaaattaaa catttaaaaa atctattaca aatgtcattt gacatgctac    2820
catgatttag tttctaatat ttactttgtt tttccaaaat ctagtcaata gtgtgcctag    2880
accatgcact caatgttaaa agcatgtagg agcatcacaa tgacaataaa atcaagataa    2940
```

```
tattttatat aatgttcata attaagcttg tcccatagac aaagattact aaataatttt   3000
aacttctcaa ataaattata atcaaatcaa tataaaggaa gaataataat gtcttttaat   3060
cacaaatgca ataatttata acctttaaaa tagtataaaa aattataaaa ataaaattta   3120
tgaaaaaaat aaatgagact taaattttt taaaaagaca aaatgtaaaa tttttacaat    3180
aaaatctact aaaaagaaat agaataattg ttttaaaaaa aataaaaatg tcattatagt   3240
tatgcaaaac tataaaggat aattgattat tttattaaaa aaataaaaat aacattttaa   3300
tataattatt tttataatta aacttttaaa aaataattat ctaaatttta aaatattatg   3360
tatattaaaa aataaaacta aaaaaaaaag ttagggggc ctcgcacctc cgtatctggc    3420
cgcaggagaa gttatcacat gagtttcgcg ccccccccc ccgccgccc cctattttt     3480 ttttctatta tttgctataa gtatttgatg gtcaatatgg agaaaagaa agagtaatta   3540 ccaattttt ttcaattcaa aaatgtagat gtccgcagcg ttattataaa atgaaagtac   3600
attttgataa aacgacaaat tacgatccgt cgtatttata ggcgaaagca ataaacaaat  3660
tattctaatt cggaaatctt tatttcgacg tgtctacatt cacgtccaaa tggggcttag  3720
gatgagaaac ttcacgattt ggcgcgccaa agcttgatat cgaattcctg cagccccctt  3780 aaagggggg atccggtccg atgtgagact tttcaacaaa gggtaatatc cggaaacctc   3840
ctcggattcc attgcccagc tatctgtcac tttattgtga agatagtgga aaggaaggt   3900 ggctcctaca aatgccatca ttgcgataaa ggaaaggcca tcgttgaaga tgcctctgcc   3960
gacagtggtc ccaaagatgg accccacc acgaggagca tcgtggaaaa agaagacgtt    4020
ccaaccacgt cttcaaagca agtggattga tgtgatggtc cgattgagac ttttcaacaa   4080
agggtaatat ccggaaacct cctcggattc cattgcccag ctatctgtca ctttattgtg   4140
aagatagtgg aaaaggaagg tggctcctac aaatgccatc attgcgataa aggaaaggcc   4200
atcgttgaag atgcctctgc cgacagtggt cccaaagatg gaccccacc acgaggagc    4260 atcgtggaaa agaagacgt tccaaccacg tcttcaaagc aagtggattg atgtgatatc    4320
tccactgacg taagggatga cgcacaatcc cactatcctt cgcaagaccc ttcctctata   4380
taaggaagtt catttcattt ggagaggacc aggtggtacc ggcgcgccac catggtgagc   4440
ttttgcgagc tttgtggtgc cgaagctgat ctccattgtg ccgcggactc tgccttcctc   4500
tgccgttctt gtgacgctaa gttccatgcc tcaaatttc tcttcgctcg tcatttccgg    4560
cgtgtcatct gcccaaattg caaatctctt actcaaaatt tcgtttctgg tcctcttctt   4620
ccttggcctc cacgaacaac atgttgttca gaatcgtcgt cttcttcttg ctgctcgtct   4680
cttgactgtg tctcaagctc cgagctatcg tcaacgacgc gtgacgtaaa cagagcgcga   4740
gggagggaaa acagagtgaa tgccaaggcc gttgcggtta cggtggcgga tggcatttt    4800 gtaaattggt gtggtaagtt aggactaaac agggatttaa caaacgctgt cgtttcatat   4860
gcgtctttgg ctttggctgt ggagacgagg ccaagagcga cgaagagagt gttcttagcg   4920
gcggcgtttt ggttcggcgt taagaacacg acgacgtggc agaatttaaa gaaagtagaa   4980
gatgtgactg gagtttcagc tgggatgatt cgagcggttg aaagcaaatt ggcgcgtgca   5040
atgacgcagc agcttagacg gtggcgcgtg gattcggagg aaggatgggc tgaaaacgac   5100
aacgtttagg cgatcgcggg ccctgatcac ctgtcgtaca gtatttctac atttgatgtg   5160
tgatttgtga agaacatcaa acaaaacaag cactggcttt aatatgatga taagtattat   5220
ggtaattaat taattggcaa aaacaacaat gaagctaaaa ttttatttat tgagccttgc   5280
ggttaatttc ttgtgatgat ctttttttt attttctaat tatatatagt ttcctttgct    5340
```

```
ttgaaatgct aaaggtttga gagagttatg ctcttttttt cttcctcttt cttttttaac     5400
tttatcatac aaattttgaa taaaaatgtg agtacattct cgagcaggac ctgcagaagc     5460
tagcttgatg gggatcagat tgtcgtttcc cgccttcagt ttaaactatc agtgtttgat     5520
ttacttaaac gaggtaattg taaaacttaa acttgatata gttaaatgtt atatatatat     5580
atatataata cttaacttat ttaattatca aaatttattt tgaaccaaac ttttactaat     5640
ttaatattaa tttattttt tgttaaaaag gcaagtaaag taataaaaaa attcataaaa     5700
tgatttaaaa ttatagagtg ataaacttat ctttttagt acataaaatt tcaaaaacgg      5760
agaccatgat gtctttagga ttaaaagta attaaaggaa aaatgtaaaa aaaaaaaagt      5820
taaggaacta aaaataagga taaaagtta agaatgttg atcaataaaa aaaagagtt       5880 caataactaa aaacaaaaat cctaaaaata ttagtgacta gtaaatacta atcttgaaca     5940
acgttctatc aataattcaa ttaaagatcg agtgaaggaa gaatgcttct ttaaaaataa     6000
actaataaag agatatatac atttcatact ttttttttatc acgtatacat ttctctctta    6060
aaaaaccata tatacatttc taaagaaaat attgcacatt tctactttca aaatacattt     6120
gacggtaaca tgtagatgga gggaaaaatt atggttttc attttatttt tagtgttaat      6180
ttatttttat tattattttt tttatcttat ttgatagcct gacattttt tgatttgttt      6240 ttttattaat tgtgtgtaaa gacaaagtat tagatttgtg caaataaact aggtcaagac     6300
taaagtttat ttaattttaa agactagact ttagatcatt taaaaaaaat tttaagtcta     6360
acatgtcaac ctatttaagt aaatgtaagt atttaatttt tgttgttatt ttttataatg     6420
gataggtatt cagttggttc aagaaccca taaccatccc tactaaatag gtatccagtc      6480 ttaccccccaa ttggcccccca caaacaggtg attaaaccca taataaaaaa agtgaattga   6540
ttaagggaaa agagaagttt aggccactta accccaatt atggaagaat tacctagacg     6600
gtaatccaag cacaaaggtc catggttcaa ggcccacaaa tgtttgtata aatagggga     6660 aaaccctaag taatgaccat tgttcgtttg atgtgcattt tattgccttg cttactactc     6720
acaattgaac tctgacttaa gcgtttgagt atcttttgca agtatccccc ccttgggtca    6780
tcttatttgg cacgtgaaga agacaaagtc caaaggcagg accttctat tagagggaca     6840 gtgtccgacc attatttggt aggaatattt tggcacccca agtaagata gtccttgacc     6900 ctaagaatta tggcaatcac acgcacaaga accaacatag cagcaaaaac caacttggga    6960
atcattagcc tgaagaagtc catgtagagg gctagattga cttatcctta atggtgagga    7020
ggctacaagc acaagtatta gatatgcgtc aacatcatgt cgaagaggtc attacccttt    7080
gacaagaaaa tgcacaacta caagagggta accgttccta gaaacccgaa atgaaacac     7140 ctgttggagc ggaggtagag tcaaccaatt ttgagatgcc aaaagccacc aatgttagtg    7200
tttggcagga tacacaccct cagttcataa atatgttagg gaagcaacta cagtagttca    7260
agaacacctt tttcctcggt gtcatggaag ccacctcct tcccaactag aagaacctca    7320
ccatcgagaa gtactatggt accactaacc catatgagca ccttgacgtt tatatcaccc    7380
aagtcagcct gtacactatg gataatgttg tcttatgcca ggtgttccct acatctttga    7440
aggggtagat cctccattag ttcacccacc tccctccccc aaca                     7484
```

<210> SEQ ID NO 7
<211> LENGTH: 100
<212> TYPE: DNA
<213> ORGANISM: Artificial sequence
<220> FEATURE:

<223> OTHER INFORMATION: 5' longer junction

<400> SEQUENCE: 7

```
cccccccgc cgcccctat ttttttttc tattatttgc tataagtatt tgatggtcaa      60
tatggagaaa aagaaagagt aattaccaat ttttttcaa                         100
```

<210> SEQ ID NO 8
<211> LENGTH: 100
<212> TYPE: DNA
<213> ORGANISM: Artificial sequence
<220> FEATURE:
<223> OTHER INFORMATION: 3' longer junction

<400> SEQUENCE: 8

```
ggggatcaga ttgtcgtttc ccgccttcag tttaaactat cagtgtttga tttacttaaa   60
cgaggtaatt gtaaaactta aacttgatat agttaaatgt                        100
```

<210> SEQ ID NO 9
<211> LENGTH: 1644
<212> TYPE: DNA
<213> ORGANISM: Artificial sequence
<220> FEATURE:
<223> OTHER INFORMATION: BBX32 cassette

<400> SEQUENCE: 9

```
ggtccgatgt gagacttttc aacaaagggt aatatccgga aacctcctcg gattccattg   60
cccagctatc tgtcacttta ttgtgaagat agtggaaaag gaaggtggct cctacaaatg  120
ccatcattgc gataaaggaa aggccatcgt tgaagatgcc tctgccgaca gtggtcccaa  180
agatggaccc ccacccacga ggagcatcgt ggaaaaagaa gacgttccaa ccacgtcttc  240
aaagcaagtg gattgatgtg atggtccgat tgagactttt caacaaaggg taatatccgg  300
aaacctcctc ggattccatt gcccagctat ctgtcacttt attgtgaaga gtggaaaaa   360
ggaaggtggc tcctacaaat gccatcattg cgataaagga aaggccatcg ttgaagatgc  420
ctctgccgac agtggtccca agatggaccc ccacccacg aggagcatcg tggaaaaga   480
agacgttcca accacgtctt caaagcaagt ggattgatgt gatatctcca ctgacgtaag  540
ggatgacgca caatcccact atccttcgca agacccttcc tctatataag gaagttcatt  600
tcatttggag aggaccaggt ggtaccggcg cgccaccatg gtgagctttt gcgagctttg  660
tggtgccgaa gctgatctcc attgtgccgc ggactctgcc ttcctctgcc gttcttgtga  720
cgctaagttc catgcctcaa attttctctt cgctcgtcat ttccggcgtg tcatctgccc  780
aaattgcaaa tctcttactc aaaatttcgt ttctggtcct cttcttcctt ggcctccacg  840
aacaacatgt tgttcagaat cgtcgtcttc ttcttgctgc tcgtctcttg actgtgtctc  900
aagctccgag ctatcgtcaa cgacgcgtga cgtaaacaga gcgcgaggga gggaaaacag  960
agtgaatgcc aaggccgttg cggttacggt ggcggatggc attttgtaa attggtgtgg  1020
taagttagga ctaaacaggg atttaacaaa cgctgtcgtt tcatatgcgt ctttggcttt  1080
ggctgtggag acgaggccaa gagcgacgaa gagagtgttc ttagcggcgg cgttttggtt  1140
cggcgttaag aacacgacga cgtggcagaa tttaaagaaa gtagaagatg tgactggagt  1200
ttcagctggg atgattcgag cggttgaaag caaattggcg cgtgcaatga cgcagcagct  1260
tagacggtgg cgcgtggatt cggaggaagg atgggctgaa aacgacaacg tttaggcgat  1320
cgcgggccct gatcacctgt cgtacagtat ttctacattt gatgtgtgat ttgtgaagaa  1380
catcaaacaa aacaagcact ggctttaata tgatgataag tattatggta attaattaat  1440
```

```
tggcaaaaac aacaatgaag ctaaaatttt atttattgag ccttgcggtt aatttcttgt    1500
gatgatcttt ttttttattt tctaattata tatagtttcc tttgctttga aatgctaaag    1560
gtttgagaga gttatgctct tttttcttc ctctttcttt tttaacttta tcatacaaat     1620
tttgaataaa aatgtgagta catt                                           1644
```

```
<210> SEQ ID NO 10
<211> LENGTH: 30
<212> TYPE: DNA
<213> ORGANISM: Artificial sequence
<220> FEATURE:
<223> OTHER INFORMATION: reverse primer for event zygosity

<400> SEQUENCE: 10
gttttacaat tacctcgttt aagtaaatca                                       30

<210> SEQ ID NO 11
<211> LENGTH: 24
<212> TYPE: DNA
<213> ORGANISM: Artificial sequence
<220> FEATURE:
<223> OTHER INFORMATION: forward primer for event zygosity

<400> SEQUENCE: 11
cattctcgag caggacctgc agaa                                             24

<210> SEQ ID NO 12
<211> LENGTH: 23
<212> TYPE: DNA
<213> ORGANISM: Artificial sequence
<220> FEATURE:
<223> OTHER INFORMATION: 6FAM-labeled probe for event zygosity

<400> SEQUENCE: 12
aacactgata gtttaaactg aag                                              23

<210> SEQ ID NO 13
<211> LENGTH: 32
<212> TYPE: DNA
<213> ORGANISM: Artificial sequence
<220> FEATURE:
<223> OTHER INFORMATION: forward primer for wild type allele

<400> SEQUENCE: 13
ctattatttg ctataagtat ttgatgtaag aa                                    32

<210> SEQ ID NO 14
<211> LENGTH: 22
<212> TYPE: DNA
<213> ORGANISM: Artificial sequence
<220> FEATURE:
<223> OTHER INFORMATION: VIC-labeled probe for wild type allele

<400> SEQUENCE: 14
ttgtattaat aacaaaaaat tg                                               22

<210> SEQ ID NO 15
<211> LENGTH: 24
<212> TYPE: DNA
<213> ORGANISM: Artificial sequence
<220> FEATURE:
<223> OTHER INFORMATION: event-specific primer for zygosity

<400> SEQUENCE: 15
```

```
gtacattctc gagcaggacc tgca                                            24

<210> SEQ ID NO 16
<211> LENGTH: 21
<212> TYPE: DNA
<213> ORGANISM: Artificial sequence
<220> FEATURE:
<223> OTHER INFORMATION: event-specific primer SQ3983

<400> SEQUENCE: 16
tgatggggat cagattgtcg t                                               21

<210> SEQ ID NO 17
<211> LENGTH: 34
<212> TYPE: DNA
<213> ORGANISM: Artificial sequence
<220> FEATURE:
<223> OTHER INFORMATION: event-specific primer SQ22982

<400> SEQUENCE: 17
actatatcaa gtttaagttt tacaattacc tcgt                                 34

<210> SEQ ID NO 18
<211> LENGTH: 22
<212> TYPE: DNA
<213> ORGANISM: Artificial sequence
<220> FEATURE:
<223> OTHER INFORMATION: event-specific probe PB10453

<400> SEQUENCE: 18
ccttcagttt aaactatcag tg                                              22

<210> SEQ ID NO 19
<211> LENGTH: 20
<212> TYPE: DNA
<213> ORGANISM: Artificial sequence
<220> FEATURE:
<223> OTHER INFORMATION: primer SQ1532 for internal control

<400> SEQUENCE: 19
ggtatccctc cagaccagca                                                 20

<210> SEQ ID NO 20
<211> LENGTH: 24
<212> TYPE: DNA
<213> ORGANISM: Artificial sequence
<220> FEATURE:
<223> OTHER INFORMATION: primer SQ1533 for internal control

<400> SEQUENCE: 20
gtggactcct tctggatgtt gtaa                                            24

<210> SEQ ID NO 21
<211> LENGTH: 29
<212> TYPE: DNA
<213> ORGANISM: Artificial sequence
<220> FEATURE:
<223> OTHER INFORMATION: VIC-labeled probe PB0359 for internal control

<400> SEQUENCE: 21
atatttgctg gaaagcagct tgaggatgg                                       29
```

SOYBEAN PLANT AND SEED CORRESPONDING TO TRANSGENIC EVENT MON87712 AND METHODS FOR DETECTION THEREOF

CROSS REFERENCE TO RELATED APPLICATIONS

This application is a Division of U.S. application Ser. No. 15/343,049 filed Nov. 3, 2016, which is a Division of U.S. application Ser. No. 13/879,238, filed Sep. 9, 2013, now U.S. Pat. No. 9,493,786, which is a 371 National Stage Entry of International Application No. PCT/US2011/055799, filed Oct. 11, 2011, which claims the benefit of U.S. Provisional Application Nos. 61/392,267 and 61/393,448, filed Oct. 12, 2010 and Oct. 15, 2010, respectively, all of which are incorporated herein by reference in their entireties.

INCORPORATION OF SEQUENCE LISTING

The sequence listing that is contained in the file named "MONS299WO.txt", which is 26.3 kilobytes as measured in Microsoft Windows operating system and was created on 5 Oct. 2011, is filed electronically herewith and incorporated herein by reference.

FIELD OF THE INVENTION

The present invention relates to transgenic soybean event MON87712 and plants comprising the event that exhibit increased yield. The invention also provides cells, plant parts, seeds, plants, commodity products related to the event, and DNA molecules that are unique to the event and were created by the insertion of transgenic DNA into the genome of a soybean plant. The invention further provides methods for detecting the presence of said soybean event nucleotide sequences in a sample, probes and primers for use in detecting nucleotide sequences that are diagnostic for the presence of said soybean event.

BACKGROUND OF THE INVENTION

Soybean (*Glycine max*) is an important crop and is a primary food source in many areas of the world. The methods of biotechnology have been applied to soybean for improvement of agronomic traits and the quality of the product. One such agronomic trait is increased yield.

Increased yield may be achieved in transgenic plants by the expression of a transgene capable of providing such increased yield. The expression of foreign genes in plants is known to be influenced by many factors, such as the regulatory elements used in the transgene cassette, the chromosomal location of the transgene insert, the proximity of any endogenous regulatory elements close to the transgene insertion site, and environmental factors such as light and temperature. For example, it has been observed that there may be a wide variation in the overall level of transgene expression or in the spatial or temporal pattern of transgene expression between similarly-produced events. For this reason, it is often necessary to screen hundreds of independent transformation events in order to ultimately identify one event useful for commercial agricultural purposes. Such an event, once identified as having the desired transgene expression, molecular characteristics and the improved trait, may then be used for introgressing the improved trait into other genetic backgrounds using plant breeding methods. The resulting progeny would contain the transgenic event and would therefore have the transgene expression characteristics for that trait of the original transformant. This may be used to produce a number of different crop varieties that comprise the improved trait and are suitably adapted to specific local growing conditions.

SUMMARY OF THE INVENTION

The present invention provides transgenic soybean plants and seeds comprising event MON87712, a representative seed sample of which have been deposited with American Type Culture Collection (ATCC) under the Accession No. PTA-10296. Plants comprising the event exhibit increased yield.

The invention provides a plant, seed, cell, progeny plant, or plant part comprising the event and commodity products derived from a plant, cell, plant part, or seed comprising event MON87712. The invention thus provides a plant, seed, cell, progeny plant, plant part, or commodity product comprising a DNA molecule having a nucleotide sequence selected from the group consisting of SEQ ID NO: 1, SEQ ID NO: 2, SEQ ID NO: 3, SEQ ID NO: 4, SEQ ID NO: 7, SEQ ID NO: 8 and SEQ ID NO: 6, and complements thereof. The invention provides a plant, seed, cell, progeny plant, or plant part comprising a recombinant DNA molecule that produces an amplicon comprising a DNA molecule of the invention, for instance in a DNA amplification method. The plant parts of the soybean comprising event MON87712 of the present invention include, but are not limited to pollen, ovule, flower, shoot, root, stem, leaf, pod and seed. Novel genetic compositions contained in the genome of a plant comprising event MON87712 and products made from a plant comprising event MON87712 such as whole or processed seed, animal feed, oil, meal, flour, food products, protein supplements, fuel products and biomass from which soybean plants comprising MON87712 have been harvested are aspects of this invention.

The invention provides DNA molecules related to event MON87712. These DNA molecules may comprise nucleotide sequences representing or derived from the junction of the transgene insertion and flanking genomic DNA of event MON87712, and/or a region of the genomic DNA flanking the inserted DNA, and/or a region of the integrated transgenic DNA flanking the insertion site, and/or a region of the integrated transgenic expression cassette, and/or a contiguous sequence of any of these regions.

In one embodiment, the invention provides a DNA molecule comprising a nucleotide sequence selected from the group consisting of SEQ ID NO: 1, SEQ ID NO: 2, SEQ ID NO: 3, SEQ ID NO: 4, SEQ ID NO: 7, SEQ ID NO: 8 and SEQ ID NO: 6, and complements thereof. In another embodiment, the DNA molecule may comprise a polynucleotide having a sequence comprising from at least about 51-100 consecutive nucleotides of a sequence selected from the group consisting of SEQ ID NO: 7 and SEQ ID NO: 8 or a polynucleotide molecule having a sequence with at least 90% identity to SEQ ID NO: 6. In yet another embodiment, the invention provides a DNA molecule comprising SEQ ID NO: 1 and SEQ ID NO: 2. According to still another embodiment, there are no more than 5000 consecutive nucleotides between the 3' end of SEQ ID NO: 1 and the 5' end of SEQ ID NO: 2, for instance, no more than 4500, 4000, 3500, 3000, 2500, 2250, 2100, 2050, 2000, or 1992 consecutive nucleotides between the 3' end of SEQ ID NO: 1 and the 5' end of SEQ ID NO: 2. According to yet another embodiment, there are no more than 5000 consecutive nucleotides between the 3' end of SEQ ID NO: 7 and the 5' end of SEQ ID NO: 8, for instance, no more than 4500, 4000, 3500, 3000, 2500, 2250, 2100, 2050, 2000, or 1914 consecutive nucleotides between the 3' end of SEQ ID NO: 7 and the 5' end of SEQ ID NO: 8. In a further embodiment, the invention provides a DNA molecule comprising SEQ ID NO: 1 or SEQ ID NO: 2 and further comprising a BBX32 coding sequence. In some embodiments, the BBX32 coding sequence is operably or genetically linked to SEQ ID NO: 1 or SEQ ID NO: 2. In other embodiments, the BBX32 coding sequence is flanked by SEQ ID NO: 1 and SEQ ID NO: 2.

The invention also provides DNA molecules useful as primers and probes diagnostic for the event. Plants, cells, plant parts, commodity products, progeny, and seeds comprising these molecules are provided.

According to one aspect of the invention, compositions and methods are provided for detecting the presence of the transgene/genomic insertion region from a novel soybean plant comprising MON87712. DNA sequences are provided that comprise at least one junction sequence of MON87712 selected from the group consisting of SEQ ID NO: 1 (corresponding to positions 3495 through 3516 of SEQ ID NO: 6, FIG. 1 [F]), SEQ ID NO: 2 (corresponding to positions 5509 through 5530 of SEQ ID NO: 6, FIG. 1 [F]), SEQ ID NO: 7 (corresponding to positions 3456 through 3555 of SEQ ID NO: 6), SEQ ID NO: 8 (corresponding to positions 5470 through 5569 of SEQ ID NO: 6), and complements thereof; wherein a junction sequence is a nucleotide sequence that spans the point at which heterologous DNA inserted into the genome is linked to the soybean cell genomic DNA and detection of this sequence in a biological sample containing soybean DNA is diagnostic for the presence of the soybean event MON87712 DNA in said sample (FIG. 1). A soybean event MON87712 and soybean seed comprising these DNA molecules is an aspect of this invention.

According to another aspect of the invention, two DNA molecules are provided for use in a DNA detection method, wherein the DNA molecules function as DNA primers when used together in an amplification reaction with a template derived from event MON87712 to produce an amplicon diagnostic for event MON87712 DNA in a sample. In one embodiment, a first and second DNA molecules comprise a polynucleotide molecule having a nucleotide sequence of sufficient length of consecutive nucleotides of SEQ ID NO: 6, or a complement thereof.

In another embodiment, the first DNA molecule comprises a polynucleotide having a nucleotide sequence of sufficient length of consecutive polynucleotide of any portion of the transgene region of the DNA molecule of SEQ ID NO: 3 or SEQ ID NO: 5 and the second DNA molecule comprises a polynucleotide of similar length of any portion of a 5' flanking soybean genomic DNA region of SEQ ID NO: 3. Any amplicon produced by DNA primers homologous or complementary to any portion of SEQ ID NO: 3 and SEQ ID NO: 5, and any amplicon that comprises SEQ ID NO: 1 or at least 51 consecutive nucleotides of SEQ ID NO: 7 is an aspect of the invention.

According to another aspect of the invention, the first DNA molecule comprises a polynucleotide having a nucleotide sequence of sufficient length of consecutive polynucleotide of any portion of the transgene region of the DNA molecule of SEQ ID NO: 4 or SEQ ID NO: 5 and the second DNA molecule comprises a polynucleotide of similar length of any portion of a 3' flanking soybean genomic DNA of SEQ ID NO: 4. Any amplicons produced by DNA primers homologous or complementary to any portion of SEQ ID NO: 4 and SEQ ID NO: 5, and any amplicon that comprises SEQ ID NO: 2 or at least 51 consecutive nucleotides of SEQ ID NO: 8 is an aspect of the invention.

The invention provides methods, compositions, and kits useful for detecting the presence of DNA derived from soybean event MON87712. Certain methods comprise (a) contacting a sample comprising DNA with a primer set that when used in a nucleic acid amplification reaction with genomic DNA from a soybean comprising event MON87712 produces an amplicon diagnostic for the event; (b) performing a nucleic acid amplification reaction thereby producing the amplicon; and (c) detecting the amplicon, wherein said amplicon comprises SEQ ID NO: 1 and/or SEQ ID NO: 2, or at least 51 consecutive nucleotides of SEQ ID NO: 7 or at least 51 consecutive nucleotides of SEQ ID NO: 8. The invention also provides a method for detection of the event by (a) contacting a sample comprising DNA with a probe that when used in a hybridization reaction with genomic DNA from the event hybridizes to a DNA molecule specific for the event; (b) subjecting the sample and probe to stringent hybridization conditions; and (c) detecting the hybridization of the probe to the DNA molecule. Kits comprising the methods and compositions of the invention useful for detecting the presence of DNA derived from the event are also provided.

Another aspect of the invention is a method of determining the zygosity of a soybean plant genome comprising soybean event MON87712 DNA in a sample comprising: a) contacting the sample with three different primers that i) when used together in a nucleic acid amplification reaction with soybean event MON87712 DNA, produces a first amplicon that is diagnostic for soybean event MON87712; and ii) when used together in a nucleic acid amplification reaction with soybean genomic DNA other than MON87712 DNA, produces a second amplicon that is diagnostic for soybean wild type genomic DNA other than event MON87712 DNA; b) performing a nucleic acid amplification reaction; and c) detecting said first amplicon and said second amplicon, wherein the presence of said first and second amplicons is diagnostic of a heterozygous genome in said sample, and wherein the presence of only said first amplicon is diagnostic of a homozygous genome in said sample. In one embodiment the primers comprise SEQ ID NO: 10, SEQ ID NO: 11 or 15, and SEQ ID NO: 13.

In one embodiment the method of determining the zygosity of a soybean comprising event MON87712, comprises (a) contacting the sample comprising soybean DNA with the primer set SEQ ID NO: 10, SEQ ID NO: 11 or SEQ ID NO: 15, SEQ ID NO: 13, and the probe set 6FAM™-labeled SEQ ID NO: 12 and VIC™-labeled SEQ ID NO: 14 that when used in a nucleic acid amplification reaction with genomic DNA from a soybean comprising event MON87712, produces a first amplicon, releasing a fluorescent signal from the combination of primers SEQ ID NO: 10 and SEQ ID NO: 11 or 15 and the 6FAM™-labeled probe (SEQ ID NO: 12) that is diagnostic for soybean event MON87712; (b) performing a nucleic acid amplification reaction, thereby producing the first amplicon; and (c) detecting said first amplicon; and (d) contacting the sample comprising soybean DNA with the primer set, SEQ ID NO: 10 and SEQ ID NO: 13, and the VIC™-labeled probe (SEQ ID NO: 14) that when used in a nucleic acid amplification reaction with genomic DNA from soybean plants produces a second amplicon, releasing a fluorescent signal that is diagnostic of wild-type soybean genomic DNA homologous to the soybean genomic region of a transgene insertion identified as soybean event MON87712; (e) performing a nucleic acid amplification reaction, thereby producing the second amplicon; and (f) detecting said second amplicon; and (g) comparing the first and the second amplicons in a sample, wherein the presence of both amplicons indicates the sample is heterozygous for the transgene insertion.

The invention further provides a method of producing a soybean plant with increased yield comprising: (a) selfing a MON87712 comprising soybean plant, thereby producing a seed; (b) growing said seed to produce a plurality of progeny plant; and (c) selecting a progeny plant that comprises MON87712 or a progeny plant with increased yield. Another aspect of the invention provides a method of producing a soybean plant with increased yield comprising: (a) crossing a MON87712 comprising soybean plant with a second soybean plant, thereby producing a seed; (b) growing said seed to produce a plurality of progeny plants; and (c) selecting a progeny plant that comprises MON87712 or a progeny plant with increased yield.

In yet another aspect, the invention provides a method of increasing yield in a crop comprising a) planting a crop plant or seed comprising event MON87712; and b) growing said crop plant or seed.

The foregoing and other aspects of the invention will become more apparent from the following detailed description.

BRIEF DESCRIPTION OF THE SEQUENCES

Figure 1:
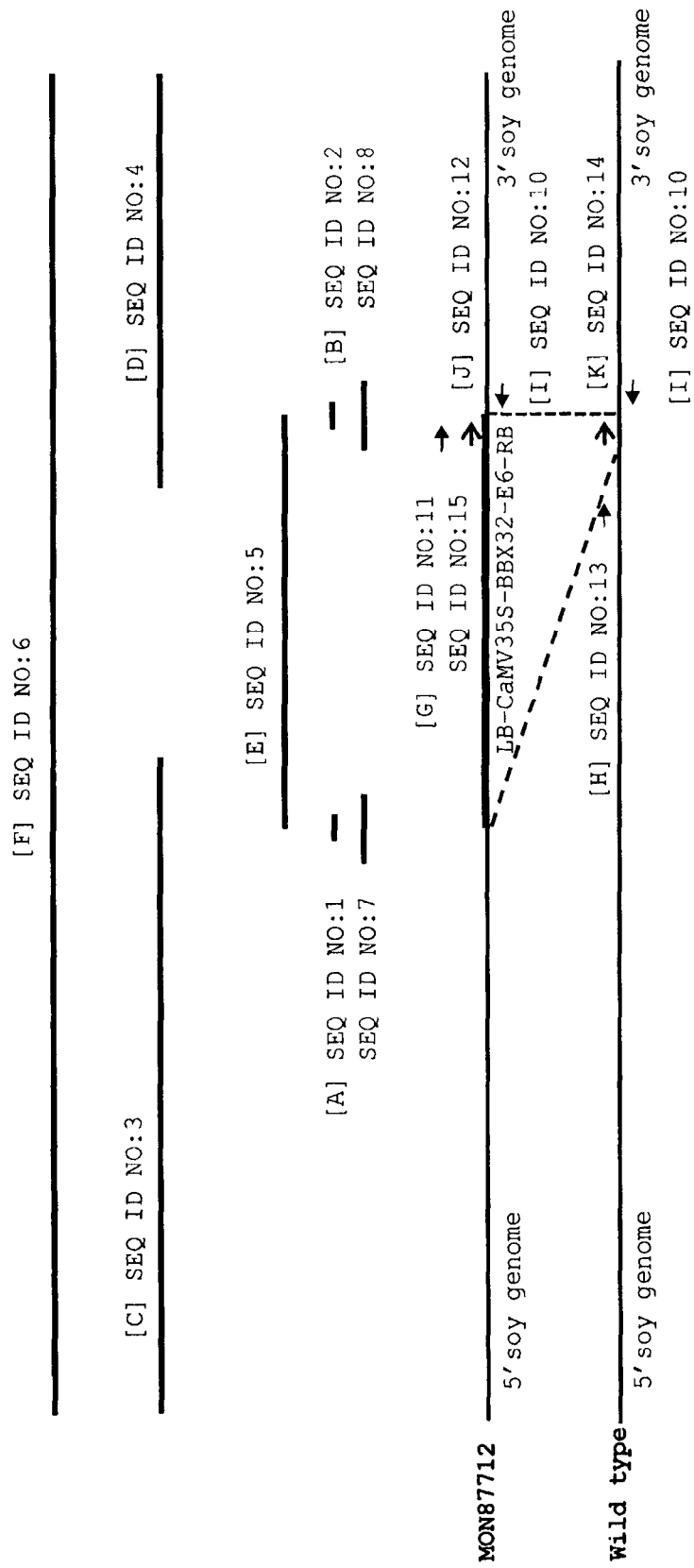
FIG. 1. Diagrammatical representation of the transgenic insert in the genome of a soybean comprising event MON87712; [A] corresponds to the relative positions of SEQ ID NO: 1 and SEQ ID NO: 7, both forming the junction between the 5' portion of the transgenic insert and the 3' portion of the flanking genomic DNA; [B] corresponds to the relative positions of SEQ ID NO: 2 and SEQ ID NO: 8, both forming the junction between the 3' portion of the transgenic insert and the 5' portion of the flanking genomic DNA; [C] corresponds to the relative position of SEQ ID NO: 3, which contains the soybean genomic flanking region and a portion of the arbitrarily designated 5' end of the transgenic DNA insert; [D] corresponds to the relative position of SEQ ID NO: 4, which contains the soybean genome flanking region and a portion of the arbitrarily designated 3' end of the transgenic DNA insert; [E] represents SEQ ID NO: 5, which is the sequence of the transgenic DNA insert including the BBX32 expression cassette integrated into the genome of a soybean plant comprising event MON87712; [F] represents SEQ ID NO: 6, which is the contiguous sequence comprising the 5' flanking genomic sequence, the transgenic insert and the 3' flanking genomic sequence, comprising as represented in the figure from left to right, SEQ ID NO: 3, SEQ ID NO: 5 and SEQ ID NO: 4, in which SEQ ID NOs: 1 and 7, and SEQ ID NOs: 2 and 8 are incorporated as set forth above, as these sequences are present in the genome of a plant comprising event MON87712; [G] and [H] represent forward primers (SEQ ID NO: 11 or SEQ ID NO: 15, and SEQ ID NO: 13) for event-specific zygosity endpoint TAQMAN® PCR for identification of MON87712 and wild-type allele, respectively; [I] represents reverse primer (SEQ ID NO: 10) for identification of MON87712 and wild-type alleles; [J] and [K] represent probes (SEQ ID NO: 12 and SEQ ID NO: 14) used for event-specific zygosity endpoint TAQMAN® PCR for identification of MON87712 and wild-type allele, respectively. Arrows indicate the direction of 5' to 3'. LB: refers to the left border of T-DNA; RB: refers to the right border of T-DNA.

SEQ ID NO: 1—A 22 bp nucleotide sequence representing the left border junction between the soybean genomic DNA and the integrated DNA insert. This sequence corresponds to positions 3495 to 3516 of SEQ ID NO: 6, and to positions 3495 through 3516 of SEQ ID NO: 3 ([C] of FIG. 1). In addition, SEQ ID NO: 1 corresponds to the integrated left border of the expression cassette at positions 1 through 11 of SEQ ID NO: 5 ([E] of FIG. 1).

SEQ ID NO: 2—A 22 bp nucleotide sequence representing the right border junction between the integrated DNA insert and the soybean genomic DNA. This sequence corresponds to positions 5509 to 5530 of SEQ ID NO: 6, and to positions 90 through 111 of SEQ ID NO: 4 ([D] of FIG. 1). In addition, SEQ ID NO: 2 corresponds to positions 2004 through 2014 SEQ ID NO: 5 ([E] of FIG. 1).

SEQ ID NO: 3—A 3605 bp nucleotide sequence including the 5' soybean genomic sequence (3505 bp) flanking the inserted DNA of event MON87712 plus a region (100 bp) of the integrated DNA. This sequence corresponds to positions 1 through 3605 of SEQ ID NO: 6. It is believed that the sequence at position 3451 to 3463 of SEQ ID NO: 3 may contain anywhere from 13 to 100 individual c residues in a row.

SEQ ID NO: 4—A 2065 bp nucleotide sequence including the 3' soybean genomic sequence (1965 bp) flanking the inserted DNA of event MON87712 plus a region (100 bp) of the integrated DNA. This sequence corresponds to positions 5420 through 7484 of SEQ ID NO: 6.

SEQ ID NO: 5—The sequence of the integrated expression cassette imparting increased yield, including the left and the right border sequences after integration. SEQ ID NO: 5 corresponds to nucleotide positions 3506 through 5519 of SEQ ID NO: 6.

SEQ ID NO: 6—A 7484 bp nucleotide sequence representing the contig of the 5' sequence flanking the inserted DNA of MON87712 (SEQ ID NO: 3), the sequence of the integrated DNA insert (SEQ ID NO: 5) and the 3' sequence flanking the inserted DNA of MON87712 (SEQ ID NO: 4). It is believed that the sequence at position 3451 to 3463 of SEQ ID NO: 6 may contain anywhere from 13 to 100 individual c residues in a row.

SEQ ID NO: 7: A 100 bp nucleotide sequence representing the left border junction between soybean genomic DNA and the integrated DNA insert. This sequence corresponds to positions 3456 to 3555 of SEQ ID NO: 6, and to positions 3456 through 3555 of SEQ ID NO: 3 ([C] of FIG. 1). In addition, SEQ ID NO: 7 corresponds to the integrated left border of the expression cassette at positions 1 through 50 of SEQ ID NO: 5 ([E] of FIG. 1).

SEQ ID NO: 8—A 100 bp nucleotide sequence representing the right border junction between the integrated DNA insert and the soybean genomic DNA. This sequence corresponds to positions 5470 to 5569 of SEQ ID NO: 6, and to positions 51 through 150 of SEQ ID NO: 4 ([D] of FIG. 1). In addition, SEQ ID NO: 8 corresponds to positions 1965 through 2014 SEQ ID NO: 5 ([E] of FIG. 1).

SEQ ID NO: 9—The nucleotide sequence of the BBX32 expression cassette of pMON83132.

SEQ ID NO: 10—The reverse primer sequence used in event-specific zygosity endpoint TAQMAN PCR assay for identification of both MON87712 DNA/allele and wild-type DNA/allele. SEQ ID NO: 10 corresponds to nucleotide positions 5517 to 5546 of SEQ ID NO: 6. Production of a PCR amplicon using the combination of primers SEQ ID NO: 10 and SEQ ID NO: 11 or 15 is a positive result for the presence of event MON87712.

SEQ ID NO: 11—The forward primer sequence used to identify MON87712 event and the zygosity of MON87712 event. SEQ ID NO: 11 corresponds to nucleotide positions 5435 to 5458 of SEQ ID NO: 6.

SEQ ID NO: 12—The probe sequence used to identify MON87712 event and the zygosity of MON87712 event. SEQ ID NO: 12 is a 6FAM™-labeled synthetic oligonucleotide. Release of a fluorescent signal in an amplification reaction using primers SEQ ID NO: 10 and SEQ ID NO: 11 or 15 in combination with the 6FAM™-labeled probe in a TAQMAN® assay is diagnostic of event MON87712.

SEQ ID NO: 13—The forward primer sequence used in event-specific zygosity endpoint TAQMAN® PCR for identification of wild-type DNA/allele. Production of a PCR amplicon using primers SEQ ID NO: 13 and SEQ ID NO: 10 is diagnostic of wild-type DNA.

SEQ ID NO: 14—The probe sequence used to determine the presence of soybean wild-type DNA/allele. SEQ ID NO: 14 is a VIC™-labeled synthetic oligonucleotide. Release of a fluorescent signal in an amplification reaction using primers SEQ ID NO: 10 and SEQ ID NO: 13 in combination with the VIC™-labeled probe in a TAQMAN® assay is diagnostic of the wild-type allele in a zygosity assay.

SEQ ID NO: 15—An alternative forward primer sequence used to identify MON87712 event and the zygosity of MON87712 event. SEQ ID NO: 15 corresponds to nucleotide positions 5432 to 5455 of SEQ ID NO: 6.

SEQ ID NO: 16—The sequence of primer SQ3983 used to identify MON87712 event. Production of a 97 bp PCR amplicon using the combination of primers SQ3983 and SQ22982 (SEQ ID NO: 17) is a positive result for the presence of event MON87712.

SEQ ID NO: 17—The sequence of primer SQ22982 used to identify MON87712 event.

SEQ ID NO: 18—The sequence of probe PB10453 used to identify MON87712 event. It is a 6FAM™-labeled synthetic oligonucleotide.

SEQ ID NO: 19—The sequence of primer SQ1532 used as an internal control in end-point TAQMAN® assays.

SEQ ID NO: 20—The sequence of primer SQ1533 used as an internal control in end-point TAQMAN® assays.

SEQ ID NO: 21—The sequence of a VIC™-labeled synthetic oligonucleotide probe PB0359 used as an internal control in end-point TAQMAN® assays.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

The present invention provides transgenic soybean event MON87712. The term "event" as used herein refers to DNA molecules produced as a result of inserting transgenic DNA into a plant's genome at a particular location on a chromosome. Event MON87712 refers to the DNA molecules produced as a result of the insertion of transgenic DNA having a sequence provided herein as SEQ ID NO: 5 into a particular chromosomal location in the *Glycine max* genome. Plants, seeds, progeny, cells, and plant parts thereof comprising event MON87712 are also provided in the present invention. A sample of seed comprising MON87712 has been deposited with American Type Culture Collection (ATCC) under Accession No. PTA-10296 on Aug. 20, 2009. Plants comprising MON87712 exhibit increased yield.

As used herein, the term "soybean" means *Glycine max* and includes all plant varieties that can be bred with soybean, including wild soybean species as well as those plants belonging to *Glycine soja* that permit breeding between species.

A transgenic "event" is produced by transformation of plant cells with heterologous DNA, i.e., a nucleic acid construct that comprises a transgene of interest, regeneration of a population of independently transformed transgenic plants resulting from the insertion of the transgene into the genome of the plant, and selection of a particular plant with desirable molecular characteristics, such as insertion of a single copy of the transgene into a particular genome location, integrity of the transgenic DNA, and an enhanced trait such as increased yield. A plant comprising the event can refer to the original transformant that includes the transgene inserted into the particular location in the plant's genome. A plant comprising the event can also refer to progeny of the original transformant that retain the transgene at the same particular location in the plant's genome. Such progeny may be produced by selfing or by a sexual outcross between the transformant, or its progeny, and another plant. Such another plant may be a transgenic plant comprising the same or a different transgene; or may be a non-transgenic plant, such as one from a different variety. The resulting progeny may be homozygous or heterozygous for event MON87712 DNA (inserted DNA and flanking DNA). Even after repeated back-crossing to a recurrent parent, the event DNA from the transformed parent is present in the progeny of the cross at the same genomic location.

A DNA molecule comprising event MON87712 refers to a DNA molecule comprising at least a portion of the inserted transgenic DNA (provided as SEQ ID NO: 5) and at least a portion of the flanking genomic DNA immediately adjacent to the inserted DNA. As such, a DNA molecule comprising event MON87712 has a nucleotide sequence representing at least a portion of the transgenic DNA insert and at least a portion of the particular region of the genome of the plant into which the transgenic DNA was inserted. The arrangement of the inserted DNA in event MON87712 in relation to the surrounding plant genome is specific and unique to event MON87712 and as such the nucleotide sequence of such a DNA molecule is diagnostic and identifying for event MON87712. Examples of the sequence of such a DNA molecule are provided herein as SEQ ID NO: 1, SEQ ID NO: 2, SEQ ID NO: 3, SEQ ID NO: 4, SEQ ID NO: 7, SEQ ID NO: 8 and SEQ ID NO: 6. Such a DNA molecule is also an integral part of the chromosome of a plant that comprises event MON87712 and may be passed on to progenies of the plant.

As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the *Glycine max* genome, which may ultimately result in the expression of a recombinant RNA and/or protein molecule in that organism. The nucleotide sequence or any fragment derived therefrom would also be considered a recombinant DNA molecule if the DNA molecule can be extracted from cells, or tissues, or homogenate from a plant or seed or plant tissue; or can be produced as an amplicon from extracted DNA or RNA from cells, or tissues, or homogenate from a plant or seed or plant tissue, any of which is derived from such materials derived from a plant comprising event MON87712. For that matter, the junction sequences as set forth at SEQ ID NO: 1, SEQ ID NO: 2, SEQ ID NO: 7 and SEQ ID NO: 8, and nucleotide sequences derived from event MON87712 that also contain these junction sequences are considered to be recombinant DNA, whether these sequences are present within the genome of the cells comprising event MON87712 or present in detectable amounts in tissues, progeny, biological samples or commodity products derived from plants comprising event MON87712. As used herein, the term "transgene" refers to a polynucleotide molecule artificially incorporated into a host cell's genome. Such transgene may be heterologous to the host cell. The term "transgenic plant" refers to a plant comprising such a transgene. A "transgenic plant" includes a plant, plant part, a plant cell or seed whose genome has been altered by the stable integration of recombinant DNA. A transgenic plant includes a plant regenerated from an originally-transformed plant cell and progeny transgenic plants from later generations or crosses of a transformed plant. As a result of such genomic alteration, the transgenic plant is distinctly different from the related wild type plant. An example of a transgenic plant is a plant described herein as comprising event MON87712.

As used herein, the term "heterologous" refers to a sequence which is not normally present in a given host genome in the genetic context in which the sequence is currently found. In this respect, the sequence may be native to the host genome, but be rearranged with respect to other genetic sequences within the host sequence.

The present invention provides DNA molecules and their corresponding nucleotide sequences. As used herein, the terms "DNA sequence", "nucleotide sequence" and "polynucleotide sequence" refer to the sequence of nucleotides of a DNA molecule, usually presented from the 5' (upstream) end to the 3' (downstream) end. The nomenclature used herein is that required by Title 37 of the United States Code of Federal Regulations § 1.822 and set forth in the tables in WIPO Standard ST.25 (1998), Appendix 2, Tables 1 and 3. The present invention is disclosed with reference to only one strand of the two nucleotide sequence strands that are provided in transgenic event MON87712. Therefore, by implication and derivation, the complementary sequences, also referred to in the art as the complete complement or the reverse complementary sequences, are within the scope of the present invention and are therefore also intended to be within the scope of the subject matter claimed.

The nucleotide sequence corresponding to the complete nucleotide sequence of the inserted transgenic DNA and substantial segments of the *Glycine max* genomic DNA flanking either end of the inserted transgenic DNA is provided herein as SEQ ID NO: 6. A subsection of this is the inserted transgenic DNA provided as SEQ ID NO: 5. The nucleotide sequence of the genomic DNA flanking the 5' end of the inserted transgenic DNA and a portion of the 5' end of the inserted DNA is provided herein as SEQ ID NO: 3. The nucleotide sequence of the genomic DNA flanking the 3' end of the inserted transgenic DNA and a portion of the 3' end of the inserted DNA is provided herein as SEQ ID NO: 4. The region spanning the location where the transgenic DNA connects to and is linked to the genomic DNA is referred to herein as the junction. A "junction sequence" or "junction region" refers to a DNA sequence and/or corresponding DNA molecule that spans the inserted transgenic DNA and the adjacent flanking genomic DNA. Examples of a junction sequence of event MON87712 are provided herein as SEQ ID NO: 1, SEQ ID NO: 2, SEQ ID NO: 7, and SEQ ID NO: 8. The identification of one of these junction sequences in a nucleotide molecule derived from a soybean plant or seed is conclusive that the DNA was obtained from event MON87712 and is diagnostic for the presence of DNA from event MON87712. SEQ ID NO: 1 is a 22 bp nucleotide sequence spanning the junction between the genomic DNA and the 5' end of the inserted DNA. SEQ ID NO: 7 is a 100 bp nucleotide sequence spanning the junction between the genomic DNA and the 5' end of the inserted DNA. SEQ ID NO: 2 is a 22 bp nucleotide sequence spanning the junction between the genomic DNA and the 3' end of the inserted DNA. SEQ ID NO: 8 is a 100 bp nucleotide sequence spanning the junction between the genomic DNA and the 3' end of the inserted DNA. Any segment of DNA derived from transgenic event MON87712 that includes the consecutive nucleotides of SEQ ID NO: 1 or 51 consecutive nucleotides, 55 consecutive nucleotides, 60 consecutive nucleotides, 65 consecutive nucleotides, 70 consecutive nucleotides, 75 consecutive nucleotides, 80 consecutive nucleotides, 85 consecutive nucleotides, 90 consecutive nucleotides, 95 consecutive nucleotides, or all of the nucleotides of SEQ ID NO: 7 is within the scope of the present invention. Any segment of DNA derived from transgenic event MON87712 that includes the consecutive nucleotides of SEQ ID NO: 2 or 51 consecutive nucleotides, 55 consecutive nucleotides, 60 consecutive nucleotides, 65 consecutive nucleotides, 70 consecutive nucleotides, 75 consecutive nucleotides, 80 consecutive nucleotides, 85 consecutive nucleotides, 90 consecutive nucleotides, 95 consecutive nucleotides, or all of the nucleotides of SEQ ID NO: 8 is within the scope of the present invention. In addition, any polynucleotide molecule comprising a sequence complementary to any of the sequences described within this paragraph is within the scope of the present invention. FIG. 1 is an illustration of the transgenic DNA insert in the genome of a soybean comprising event MON87712, and the relative positions of SEQ ID NOs: 1-8 arranged 5' to 3'. The present invention also provides a nucleic acid molecule comprising a polynucleotide having a sequence that is at least 90%, 91%, 92%, 93%, 94%, 95%, 96%, 97%, 98%, or 99% identical to the full-length of SEQ ID NO: 6.

The present invention further provides exemplary DNA molecules that can be used either as primers or probes for diagnosing the presence of DNA derived from event MON87712 in a sample. Such primers or probes are specific for a target nucleic acid sequence and as such are useful for the identification of event MON87712 nucleic acid sequence by the methods of the invention described herein.

A "probe" is an isolated nucleic acid to which is attached a detectable label or reporter molecule, e.g., a radioactive isotope, ligand, chemiluminescent agent, or enzyme. Such a probe is complementary to a strand of a target nucleic acid, in the case of the present invention, to a strand of genomic DNA from a soybean comprising event MON87712 whether from a soybean plant or from a sample that comprises DNA from the event. Probes according to the present invention include not only deoxyribonucleic or ribonucleic acids but also polyamides and other probe materials that bind specifically to a target DNA sequence and the detection of such binding can be used to diagnose/determine/confirm the presence of that target DNA sequence in a particular sample.

A "primer" is typically an isolated polynucleotide that is designed for use in specific annealing or hybridization methods to hybridize to a complementary target DNA strand to form a hybrid between the primer and the target DNA strand, and then extended along the target DNA strand by a polymerase, e.g., a DNA polymerase. A pair of primers may be used with template DNA, such as a sample of *Glycine max* genomic DNA, in a thermal or isothermal amplification, such as polymerase chain reaction (PCR), or other nucleic acid amplification methods, to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques, i.e. the product of an amplification reaction. In one embodiment of the invention, an amplicon diagnostic for event MON87712 comprises a sequence not naturally found in the *Glycine max* genome. Primer pairs, as used in the present invention, are intended to refer to use of two primers binding opposite strands of a double stranded nucleotide segment for the purpose of amplifying linearly the polynucleotide segment between the positions targeted for binding by the individual members of the primer pair, typically in a thermal or isothermal amplification reaction or other nucleic acid amplification methods. Exemplary DNA molecules useful as primers are provided as SEQ ID NOs: 10-11, SEQ ID NO: 13 and SEQ ID NO: 15. The primer pair provided as SEQ ID NO: 10 and SEQ ID NO: 11 or 15 may be used as a first DNA molecule and a second DNA molecule that is different from the first DNA molecule, and both molecules are each of sufficient length of consecutive nucleotides of either SEQ ID NO: 4, SEQ ID NO: 5, or SEQ ID NO: 6 or the complements thereof to function as DNA primers so that, when used together in an amplification reaction with template DNA derived from event MON87712, an amplicon that is specific and unique to transgenic event MON87712 would be produced. The use of the term "amplicon" specifically excludes primer-dimers that may be formed in the DNA amplification reaction.

Probes and primers according to the present invention may have complete sequence identity to the target sequence, although primers and probes differing from the target sequence that retain the ability to hybridize preferentially to target sequences may be designed by conventional methods. In order for a nucleic acid molecule to serve as a primer or probe it needs only be sufficiently complementary in sequence to be able to form a stable double-stranded structure under the particular solvent and salt concentrations employed. Any nucleic acid hybridization or amplification method can be used to identify the presence of transgenic DNA from event MON87712 in a sample. Probes and primers are generally at least about 11 nucleotides, at least about 18 nucleotides, at least about 24 nucleotides, and at least about 30 nucleotides or more in length. Such probes and primers hybridize specifically to a target sequence under high stringency hybridization conditions.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm the disclosed sequences by known methods, e.g., by re-cloning and sequencing such sequences.

The nucleic acid probes and primers of the present invention hybridize under stringent conditions to a target DNA sequence. Any nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least "low-stringency" conditions. Similarly, the molecules are said to be "complementary" if they can hybridize to one another with sufficient stability to permit them to remain annealed to one another under "high-stringency" conditions. Stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In one embodiment, a nucleic acid of the present invention will specifically hybridize to one or more of the nucleic acid molecules set forth in SEQ ID NO: 1, SEQ ID NO: 2, SEQ ID NO: 7 and SEQ ID NO: 8, or complements or fragments thereof under high stringency conditions. The hybridization of the probe to the target DNA molecule can be detected by any number of methods known to those skilled in the art. These can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA amplification reaction. Examples of DNA amplification methods include PCR, Recombinase Polymerase Amplification (RPA) (see for example U.S. Pat. No. 7,485,428), Strand Displacement Amplification (SDA) (see for example, U.S. Pat. Nos. 5,455,166 and 5,470,723), Transcription-Mediated Amplification (TMA) (see for example, Guatelli et al., *Proc. Natl. Acad. Sci. USA* 87:1874-1878 (1990)), Rolling Circle Amplification (RCA) (see for example, Fire and Xu, *Proc. Natl. Acad Sci. USA* 92:4641-4645 (1995); Lui, et al., *J. Am. Chem. Soc.* 118:1587-1594 (1996); Lizardi, et al., *Nature Genetics* 19:225-232 (1998), U.S. Pat. Nos. 5,714,320 and 6,235,502)), Helicase Dependant Amplification (HDA) (see for example Vincent et al., *EMBO Reports* 5(8): 795-800 (2004); U.S. Pat. No. 7,282,328), and Multiple Displacement Amplification (MDA) (see for example Dean et. al., *Proc. Natl. Acad Sci. USA* 99:5261-5266 (2002)).

The term "specific for (a target sequence)" indicates that a probe or primer hybridizes under stringent hybridization conditions only to the target sequence in a sample comprising the target sequence.

As used herein, the term "isolated" refers to at least partially separating a molecule from other molecules normally associated with it in its native or natural state. In one embodiment, the term "isolated" refers to a DNA molecule that is at least partially separated from the nucleic acids that normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragments thereof, can also be obtained by other techniques such as by directly synthesizing the fragment by chemical means, as is commonly practiced by using an automated oligonucleotide synthesizer.

It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the transgenic crop plants.

The presence of a transgene may be detected by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different transformation events, particularly those produced using the same DNA construct unless the sequence of chromosomal DNA adjacent to the inserted DNA ("flanking DNA") is known. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event GT73 was demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

The DNA molecules and corresponding nucleotide sequences provided herein are therefore useful for, among other things, identifying event MON87712, selecting plant varieties or hybrids comprising event MON87712, detecting the presence of DNA derived from event MON87712 in a sample, and monitoring samples for the presence and/or absence of event MON87712 or plants and plant parts comprising event MON87712.

The present invention provides plants, progeny, seeds, plant cells, plant parts (such as pollen, ovule, pod, flower, root or stem tissue, fibers, and leaf), and commodity products. These plants, progeny, seeds, plant cells, plant parts, and commodity products contain a detectable amount of a polynucleotide of the present invention, i.e., such as a polynucleotide comprising at least one of the sequences provided as the consecutive nucleotides of SEQ ID NO: 1, the consecutive nucleotides of SEQ ID NO: 2, at least 51 consecutive nucleotides of SEQ ID NO: 7, or at least 51 consecutive nucleotides of SEQ ID NO: 8. Plants, progeny, seeds, plant cells, plant parts and commodity products of the present invention may also contain one or more additional transgenes. Such transgene may be any nucleotide sequence encoding a protein or RNA molecule conferring a desirable trait including but not limited to increased insect resistance, increased water use efficiency or drought tolerance, increased yield performance, increased nitrogen use efficiency or increase tolerance to nitrogen stress such as high or low nitrogen supply, increased seed quality, increased disease resistance, improved nutritional quality, and/or increased herbicide tolerance, such as glyphosate or dicamba tolerance, in which the desirable trait is measured with respect to a comparable plant lacking such additional transgene.

The present invention provides plants, progeny, seeds, plant cells, and plant part such as pollen, ovule, pod, flower, root or stem tissue, and leaf derived from a transgenic plant comprising event MON87712. A representative sample of seed comprising event MON87712 has been deposited according to the Budapest Treaty for the purpose of enabling the present invention. The repository selected for receiving the deposit is the American Type Culture Collection (ATCC) having an address at 10801 University Boulevard, Manassas, Va. USA, Zip Code 20110. The ATCC repository has assigned the accession No. PTA-10296 to event MON87712 containing seed.

The present invention provides a microorganism comprising a DNA molecule having a nucleotide sequence selected from the group consisting of the consecutive nucleotides of SEQ ID NO: 1, the consecutive nucleotides of SEQ ID NO: 2, or at least 51 consecutive nucleotides of SEQ ID NO: 7, or of SEQ ID NO: 8 present in its genome. An example of such a microorganism is a transgenic plant cell. Microorganisms, such as a plant cell of the present invention, are useful in many industrial applications, including but not limited to: (i) use as research tool for scientific inquiry or industrial research; (ii) use in culture for producing endogenous or recombinant carbohydrate, lipid, nucleic acid, enzymes or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the present invention is a method of using a microorganism of the present invention. Methods of using microorganisms of the present invention, such as transgenic plant cells, include (i) methods of producing transgenic cells by integrating recombinant DNA into genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, enzymes or protein products from cultured cells; and (iv) methods of using modern plant tissue culture techniques with transgenic plant cells to produce transgenic plants or transgenic plant tissue cultures.

As used herein, "progeny" includes any plant, seed, plant cell, and/or regenerable plant part comprising the event DNA derived from an ancestor plant and/or a polynucleotide having at least one of the sequences provided as the consecutive nucleotides of SEQ ID NO: 1, the consecutive nucleotides of SEQ ID NO: 2, or at least 51 consecutive nucleotides of SEQ ID NO: 7, or at least 51 consecutive nucleotides of SEQ ID NO: 8. Plants, progeny, and seeds may be homozygous or heterozygous for the transgene. Progeny may be grown from seeds produced by a plant comprising event MON87712 and/or from seeds produced by a plant fertilized with pollen from a plant comprising event MON87712.

Progeny plants may be self-pollinated (also known as "selfing") to generate a true breeding line of plants, i.e., plants homozygous for the transgene. Alternatively, progeny plants may be outcrossed, e.g., bred with another plant, to produce a varietal or a hybrid seed or plant. The other plant may be transgenic or nontransgenic. A varietal or hybrid seed or plant of the present invention may thus be derived by crossing a first parent that lacks the specific and unique DNA of event MON87712 with a second parent comprising event MON87712, resulting in a hybrid comprising the specific and unique DNA of event MON87712. Each parent can be a hybrid or an inbred/variety, so long as the cross or breeding results in a plant or seed of the present invention, i.e., a seed having at least one allele comprising the specific and unique DNA of event MON87712 and/or the consecutive nucleotides of SEQ ID NO: 1 or SEQ ID NO: 2, at least 51 consecutive nucleotides of SEQ ID NO: 7 or at least 51 consecutive nucleotides of SEQ ID NO: 8. Two different transgenic plants may thus be mated to produce hybrid offspring that contain two independently segregating, added, exogenous genes. For example, a plant comprising event MON87712 with increased yield can be crossed with another transgenic plant, such as one tolerant to glyphosate, to produce a plant having the characteristics of both transgenic parents. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987). Sexually crossing one plant with another plant, i.e., cross-pollinating, may be accomplished or facilitated by human intervention, for example: by human hands collecting the pollen of one plant and contacting this pollen with the style or stigma of a second plant; by human hands and/or human actions removing, destroying, or covering the stamen or anthers of a plant (e.g., by manual intervention or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma; by selective placement of plants (e.g., intentionally planting plants in pollinating proximity); and/or by application of chemicals to precipitate flowering or to foster receptivity (of the stigma for pollen).

In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by detasseling or by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

The present invention provides a plant part that is derived from a plant comprising event MON87712. As used herein, a "plant part" refers to any part of a plant that is comprised of material derived from a plant comprising event MON87712. Plant parts include but are not limited to cells, pollen, ovule, pod, flower, root or stem tissue, fibers, and leaf. Plant parts may be viable, nonviable, regenerable, and/or non-regenerable.

The present invention provides a commodity product that is derived from a plant comprising event MON87712. As used herein, a "commodity product" refers to any composition or product that is comprised of material derived from a plant, seed, plant cell, or plant part comprising event MON87712. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, and any other food for human consumption; and biomasses and fuel products. Processed soybeans are the largest source of protein feed and vegetable oil in the world. Soybeans and soybean oils from plants comprising MON87712 can be used in the manufacture of many different products, not limited to, nontoxic plastics, printing inks, lubricants, waxes, hydraulic fluids, electric transformer fluids, solvents, cosmetics, and hair care products. Soybeans and oils of plants comprising MON87712 can be suitable for use in a variety of soy foods made from whole soybeans, such as soymilk, soy nut butter, natto, and tempeh, and soy foods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamame. Soymilk, which is typically produced by soaking and grinding whole soybeans, may be consumed without other processing, spray-dried, or processed to form soy yogurt, soy cheese, tofu, or yuba. Viable commodity products include but are not limited to seeds and plant cells. A plant comprising event MON87712 can thus be used to manufacture any commodity product typically acquired from a soybean plant. Any such commodity product that is derived from the plants comprising event MON87712 may contain at least a detectable amount of the specific and unique DNA corresponding to event MON87712, and specifically may contain a detectable amount of a polynucleotide having a nucleotide sequence of the consecutive nucleotides of SEQ ID NO: 1, the consecutive nucleotides of SEQ ID NO: 2, at least 51 consecutive nucleotides of SEQ ID NO: 7 or at least 51 consecutive nucleotides of SEQ ID NO: 8. Any standard method of detection for polynucleotide molecules may be used, including methods of detection disclosed herein. A commodity product is within the scope of the present invention if there is any detectable amount of the consecutive nucleotides of SEQ ID NO: 1, the consecutive nucleotides of SEQ ID NO: 2, at least 51 consecutive nucleotides of SEQ ID NO: 7 or at least 51 consecutive nucleotides of SEQ ID NO: 8 in the commodity product.

The plant, progeny, seed, plant cell, plant part (such as pollen, ovule, pod, flower, root or stem tissue, and leaf), and commodity products of the present invention are therefore useful for, among other things, growing plants for the purpose of producing seed and/or plant parts comprising event MON87712 for agricultural purposes, producing progeny comprising event MON87712 for plant breeding and research purposes, use with microbiological techniques for industrial and research applications, and sale to consumers.

The present invention provides methods for producing plants with increased yield and plants comprising event MON87712. An event MON87712 containing plant was produced by an *Agrobacterium* mediated transformation method similar to that described in U.S. Pat. No. 5,914,451, using an inbred soybean line with the construct pMON83132 (Table 1). Construct pMON83132 contains a plant expression cassette for expression of the BBX32 protein in soybean plant cells. Transgenic soybean cells were regenerated into intact soybean plants and individual plants were selected from the population of independently transformed transgenic plants that showed desirable molecular characteristics, such as single copy of the transgene cassette at a single locus, the integrity of the transgene cassette, absence of the construct backbone sequence, loss of the unlinked glyphosate resistance selection cassette. Furthermore, inverse PCR and DNA sequence analyses were performed to determine the 5' and 3' insert-to-plant genome junctions, to confirm the organization of the elements within the insert (FIG. 1), and to determine the complete DNA sequence of the insert in soybean event MON87712 (SEQ ID NO: 5). In addition, transgenic plants were screened and selected for increased yield under field conditions. A soybean plant that contains in its genome the BBX32 expression cassette of pMON83132 is an aspect of the present invention.

Increased yield of a transgenic plant of the present invention can be measured in a number of ways, including test weight, seed number per plant, seed weight, seed number per unit area (i.e. seeds, or weight of seeds, per acre), bushels per acre, tons per acre, or kilo per hectare. Expression of the BBX32 protein in plants comprising event MON87712 leads to an increase in yield brought about by the increased capacity for growth and reproductive development. Increased yield results from the partitioning of growth in one or more of the yield parameters including more seeds per plot, larger seeds, more seeds per plant, and/or more plants per plot. Recombinant DNA used in this invention provides increased yield through an increase in source compounds when compared to non-transgenic soybean with the same genetic background. These biochemical and metabolic changes are linked to diurnally-regulated pathways that are impacted by the activity of BBX32 and include carbon metabolism and nitrogen metabolism.

Methods for producing a plant with increased yield comprising transgenic event MON87712 are provided. Transgenic plants used in these methods may be homozygous or heterozygous for the transgene. Progeny plants produced by these methods may be varietal or hybrid plants; may be grown from seeds produced by a plant and/or from seed comprising event MON87712 produced by a plant fertilized with pollen from a plant comprising event MON87712; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant. As used herein, the term "zygosity" refers to the similarity of DNA at a specific chromosomal location (locus) in a plant. In the present invention, the DNA specifically refers to the transgene insert along with the junction sequence (event DNA). A plant is homozygous if the transgene insert with the junction sequence is present at the same location on each chromosome of a chromosome pair (2 alleles). A plant is considered heterozygous if the transgene insert with the junction sequence is present on only one chromosome of a chromosome pair (1 allele). A wild-type plant is null for the event DNA.

A plant with increased yield may be produced by sexually crossing a plant comprising event MON87712 comprising a polynucleotide having the nucleotide sequence of consecutive nucleotides of SEQ ID NO: 1, a polynucleotide having the nucleotide sequence of consecutive nucleotides of SEQ ID NO: 2, at least 51 consecutive nucleotides of SEQ ID NO: 7, and/or at least 51 consecutive nucleotides of SEQ ID NO: 8 with another plant and thereby producing seed, which is then grown into progeny plants. These progeny plants may be analyzed using diagnostic methods to select for progeny plants that contain event MON87712 DNA or for progeny plants with increased yield. The other plant used may or may not be transgenic. The progeny plant and/or seed produced may be varietal or hybrid seed.

A plant with increased yield may be produced by selfing a plant comprising event MON87712 comprising a polynucleotide having the nucleotide sequence of consecutive nucleotides of SEQ ID NO: 1, a polynucleotide having the nucleotide sequence of consecutive nucleotides of SEQ ID NO: 2, at least 51 consecutive nucleotides of SEQ ID NO: 7, and/or at least 51 consecutive nucleotides of SEQ ID NO: 8 and thereby producing seed, which is then grown into progeny plants. These progeny plants may then be analyzed using diagnostic methods to select for progeny plants that comprise event MON87712 DNA.

Progeny plants and seeds encompassed by these methods and produced by using these methods are distinct from other plants, for example, because the progeny plants and seeds are recombinant and as such created by human intervention; contain at least one allele that consists of the transgenic DNA of the present invention; and/or contain a detectable amount of a polynucleotide sequence selected from the group consisting of consecutive nucleotides of SEQ ID NO: 1, consecutive nucleotides of SEQ ID NO: 2, at least 51 consecutive nucleotides of SEQ ID NO: 7, and at least 51 consecutive nucleotides of SEQ ID NO: 8. A seed may be selected from an individual progeny plant, and so long as the seed comprises SEQ ID NO: 1, SEQ ID NO: 2, at least 51 consecutive nucleotides of SEQ ID NO: 7, and/or at least 51 consecutive nucleotides of SEQ ID NO: 8, it will be within the scope of the present invention.

The plants, progeny, seeds, plant cells, plant parts (such as pollen, ovule, pod, flower, root or stem tissue, and leaves), and commodity products of the present invention may be evaluated for DNA composition, gene expression, and/or protein expression. Such evaluation may be done by using various methods such as PCR, sequencing, northern blotting, southern analysis, western blotting, immuno-precipitation, and ELISA or by using the methods of detection and/or the detection kits provided herein.

Methods of detecting the presence of compositions specific to event MON87712 in a sample are provided. One method consists of detecting the presence of DNA specific to and derived from a cell, a tissue, a seed, a plant or plant parts comprising event MON87712. The method provides for a template DNA sample to be contacted with a primer pair that is capable of producing an amplicon from event MON87712 DNA upon being subjected to conditions appropriate for amplification, particularly an amplicon that comprises SEQ ID NO: 1, SEQ ID NO: 2, at least 51 consecutive nucleotides of SEQ ID NO: 7, and/or at least 51 consecutive nucleotides of SEQ ID NO: 8, or the complements thereof. The amplicon is produced from a template DNA molecule derived from event MON87712, so long as the template DNA molecule incorporates the specific and unique nucleotide sequences of SEQ ID NO: 1, SEQ ID NO: 2, at least 51 consecutive nucleotides of SEQ ID NO: 7, and/or at least 51 consecutive nucleotides of SEQ ID NO: 8. The amplicon may be single or double stranded DNA or RNA, depending on the polymerase selected for use in the production of the amplicon. The method provides for detecting the amplicon molecule produced in any such amplification reaction, and confirming within the sequence of the amplicon the presence of the nucleotides corresponding to SEQ ID NO: 1, SEQ ID NO: 2, at least 51 consecutive nucleotides of SEQ ID NO: 7, and/or at least 51 consecutive nucleotides of SEQ ID NO: 8, or the complements thereof. The detection of the nucleotides corresponding to SEQ ID NO: 1, SEQ ID NO: 2, at least 51 consecutive nucleotides of SEQ ID NO: 7, and/or at least 51 consecutive nucleotides of SEQ ID NO: 8, or the complements thereof in the amplicon are determinative and/or diagnostic for the presence of event MON87712 specific DNA and thus biological material comprising event MON87712 in the sample.

Another method is provided for detecting the presence of a DNA molecule corresponding to SEQ ID NO: 3 or SEQ ID NO: 4 in a sample consisting of material derived from plant or plant tissue. The method consists of (i) obtaining a DNA sample from a plant, or from a group of different plants, (ii) contacting the DNA sample with a DNA probe molecule comprising the nucleotides as set forth in either SEQ ID NO: 1 or SEQ ID NO: 2, (iii) allowing the probe and the DNA sample to hybridize under stringent hybridization conditions, and then (iv) detecting a hybridization event between the probe and the target DNA sample. Detection of the hybrid composition is diagnostic for the presence of SEQ ID NO: 3 or SEQ ID NO: 4, as the case may be, in the DNA sample. Absence of hybridization is alternatively diagnostic of the absence of the transgenic event in the sample if the appropriate positive controls are run concurrently. Alternatively, determining that a particular plant contains either or both of the sequences corresponding to SEQ ID NO: 1 or SEQ ID NO: 2, or the complements thereof, is determinative that the plant contains at least one allele corresponding to event MON87712.

It is thus possible to detect the presence of a nucleic acid molecule of the present invention by any well known nucleic acid amplification and detection methods such as polymerase chain reaction (PCR), recombinase polymerase amplification (RPA), or DNA hybridization using nucleic acid probes. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for transgenic event RT73 is demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

DNA detection kits are provided. One type of kit contains at least one DNA molecule of sufficient length of contiguous nucleotides of SEQ ID NO: 3, SEQ ID NO: 5, or SEQ ID NO: 6 to function as a DNA primer or probe specific for detecting the presence of DNA derived from transgenic event MON87712 in a sample. The DNA molecule being detected with the kit comprises contiguous nucleotides of the sequence as set forth in SEQ ID NO: 1 or at least 51 consecutive nucleotides of SEQ ID NO: 7. Alternatively, the kit may contain at least one DNA molecule of sufficient length of contiguous nucleotides of SEQ ID NO: 4, SEQ ID NO: 5, or SEQ ID NO: 6 to function as a DNA primer or probe specific for detecting the presence of DNA derived from transgenic event MON87712 in a sample. The DNA molecule being detected with the kit comprises contiguous nucleotides as set forth in SEQ ID NO: 2 or at least 51 consecutive nucleotides of SEQ ID NO: 8.

An alternative kit employs a method in which the target DNA sample is contacted with a primer pair as described above, then performing a nucleic acid amplification reaction sufficient to produce an amplicon comprising the consecutive nucleotides of SEQ ID NO: 1, SEQ ID NO: 2, at least 51 consecutive nucleotides of SEQ ID NO: 7, or at least 51 consecutive nucleotides of SEQ ID NO: 8. Detection of the amplicon and determining the presence of the consecutive nucleotides of SEQ ID NO: 1, SEQ ID NO: 2, at least 51 consecutive nucleotides of SEQ ID NO: 7, or at least 51 consecutive nucleotides of SEQ ID NO: 8, or the complements thereof within the sequence of the amplicon is diagnostic for the presence of event MON87712 specific DNA in a DNA sample.

A DNA molecule sufficient for use as a DNA probe is provided that is useful for determining, detecting, or for diagnosing the presence or even the absence of DNA specific and unique to event MON87712 DNA in a sample. The DNA molecule contains the consecutive nucleotides of SEQ ID NO: 1, or the complement thereof, the consecutive nucleotides of SEQ ID NO: 2, or the complement thereof, at least 51 consecutive nucleotides of SEQ ID NO: 7, or the complement thereof, or at least 51 consecutive nucleotides of SEQ ID NO: 8, or the complement thereof.

Nucleic acid amplification can be accomplished by any of the various nucleic acid amplification methods known in the art, including thermal and isothermal amplification methods. The sequence of the heterologous DNA insert, junction sequences, or flanking sequences from event MON87712 (with representative seed samples comprising event MON87712 deposited as ATCC PTA-10296) can be verified by amplifying such sequences from the event using primers derived from the sequences provided herein followed by standard DNA sequencing of the amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed which overlaps both the adjacent flanking genomic DNA sequence and the inserted DNA sequence. The oligonucleotide is immobilized in wells of a microwell plate. Following thermal amplification of the region of interest (using one primer in the inserted sequence and one in the adjacent flanking genomic sequence), a single-stranded amplicon can be hybridized to the immobilized oligonucleotide and serve as a template for a single base extension reaction using a DNA polymerase and labelled ddNTPs specific for the expected next base. Readout may be fluorescent or ELISA-based. Detection of a fluorescent or other signal indicates the presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to a single-stranded amplicon from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. ddNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon. Using this method an oligonucleotide is designed which overlaps the genomic flanking and inserted DNA junction. The oligonucleotide is hybridized to single-stranded amplicon from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) may also be used to detect and/or quantifying the presence of a DNA sequence using the instructions provided by the manufacturer. Briefly, a FRET oligonucleotide probe is designed which overlaps the genomic flanking and insert DNA junction. The FRET probe and amplification primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and amplification primers (one primer in the insert DNA sequence and one in the flanking genomic sequence) are cycled in the presence of a thermostable polymerase and dNTPs. Following successful amplification, hybridization of the FRET probe to the target sequence results in the removal of the probe secondary structure and spatial separation of the fluorescent and quenching moieties, which leads to the production of a fluorescent signal. The fluorescent signal indicates the presence of the flanking/transgene insert sequence due to successful amplification and hybridization.

Other described methods, such as, microfluidics (US Patent Publication No. 2006068398, U.S. Pat. No. 6,544,734) provide methods and devices to separate and amplify DNA samples. Optical dyes are used to detect and measure specific DNA molecules (WO/05017181). Nanotube devices (WO/06024023) that comprise an electronic sensor for the detection of DNA molecules or nanobeads that bind specific DNA molecules and can then be detected.

DNA detection kits can be developed using the compositions disclosed herein and the methods well known in the art of DNA detection. The kits are useful for the identification of event MON87712 in a sample and can be applied to methods for breeding plants containing the appropriate event DNA. The kits may contain DNA primers or probes that are similar or complementary to SEQ ID NO: 1-6, or fragments or complements thereof.

The kits and detection methods of the present invention are therefore useful for, among other things, identifying event MON87712, selecting plant varieties or hybrids comprising event MON87712, detecting the presence of DNA derived from event MON87712 in a sample, and monitoring samples for the presence and/or absence of event MON87712 or plants, plant parts or commodity products comprising event MON87712.

The following examples are included to demonstrate examples of certain embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1: Transformation of Soybean with pMON83132 and Event Selection

This example describes transformation and generation of transgenic soybean events, and selection of event MON87712.

An *Agrobacterium*-mediated transformation method was used to transform soybean cells with a binary construct designated as pMON83132. The construct contains two plant transformation cassettes or T-DNAs. Each cassette is flanked by right border and left border sequences. The transgenic insert as set forth in SEQ ID NO: 5 comprises a transformation cassette containing an enhanced 35S promoter from cauliflower mosaic virus (CaMV), operably linked to a DNA molecule encoding BBX32 protein, operably linked to the 3' untranslated region from fiber protein E6 gene of *Gossypium barbadense* (cotton). The second transformation cassette contains a chimeric promoter consisting of enhancer sequences from the promoter of the figwort mosaic virus (FMV) 35S RNA combined with the promoter of the EF-1α gene from *Arabidopsis thaliana* that encodes elongation factor EF-1 alpha. It also contains a leader (exon 1) and intron with flanking splice sites of the *Arabidopsis* EF-1α gene, operably linked to a DNA molecule encoding a chloroplast transit peptide (CTP2) from *Arabidopsis* EPSP synthase, fused to a codon modified coding sequence of the aroA gene from the *Agrobacterium* sp. strain CP4 encoding the CP4 EPSPS protein, operably linked to a 3' untranslated region of the RbcS2 gene from *Pisum sativum*. The CP4 aroA gene confers tolerance to glyphosate, and was used as a selectable marker. Table 1 is a summary of the genetic elements in pMON83132.

After transformation with construct pMON83132, transformed cells were allowed to grow and multiply on media containing glyphosate. Plants were regenerated from surviving cells. A total of 4944 independent R0 transformation events were produced and characterized by detailed molecular analyses. Events were screened by quantitative PCR and RT-PCR (TAQMAN®) for insert number (number of integration sites within the soybean genome), copy number (the number of copies of the T-DNA within one locus), the integrity of the inserted cassette and the absence of backbone sequence, and expression of the AtBBX32 transgene transcript. Events with undesirable molecular characteristics, such as presence of multiple copies of the transgene and/or molecular complexity of the insert, the presence of the transformation vector backbone sequence were eliminated. Furthermore, linkage Southern analysis was done to remove events where the BBX32 expression cassette was linked to the CP4 selectable marker cassette. A total of 284 events met the stringent molecular selection criteria based on the analyses described above. Three additional events were further eliminated due to unavailability of homozygous seed stocks, resulting in 281 events being advanced to R1 generation.

TABLE 1

Summary of the genetic elements in pMON83132.

| Genetic Element | Location in Construct pMON83132 | Function (Reference) |
|---|---|---|
| T-DNA I | | |
| B[1]-Left Border | 1-442 | DNA region from *Agrobacterium tumefaciens* containing the left border sequence used for transfer of the T-DNA (Barker et al., Plant Mol. Biol. 2: 335-350, 1983). |
| P[2]-e35S | 511-1123 | Promoter for the cauliflower mosaic virus (CaMV) 35S RNA (Odell et al., Nature 313: 810-812, 1985) containing the duplicated enhancer region (Kay et al., Science 236: 1299-1302, 1987) that directs transcription in plant cells. |
| CS[3]-BBX32 | 1148-1825 | Coding sequence of the BBX32 gene from *Arabidopsis thaliana* encoding a zinc finger protein (B-box type) (Khanna et al., Plant Cell 21: 3416-3420, 2009) which modulates aspects of diurnal biology (Holtan et al., submitted). |
| T[4]-E6 | 1840-2154 | 3' UTR region of the E6 gene of *Gossypium barbadense* (cotton) that encodes a fiber protein involved in early fiber development (John, Plant Mol Biol. 30: 297-306, 1996) which functions to direct polyadenylation of mRNA. |

TABLE 1-continued

Summary of the genetic elements in pMON83132.

| Genetic Element | Location in Construct pMON83132 | Function (Reference) |
|---|---|---|
| B-Right Border | 2193-2549 | DNA region from *Agrobacterium tumefaciens* containing the right border sequence used for transfer of the T-DNA (Depicker et al., J. of Mol. and Applied Genetics 1: 561-573, 1982; Zambryski et al., J. of Mol. and Applied Genetics 1: 361-370, 1982). |

T-DNA II

| Genetic Element | Location | Function (Reference) |
|---|---|---|
| B-Right Border | 2721-3077 | DNA region from *Agrobacterium tumefaciens* containing the right border sequence used for transfer of the T-DNA (Depicker et al., J. of Mol. and Applied Genetics 1: 561-573, 1982; Zambryski et al., J. of Mol. and Applied Genetics 1: 361-370, 1982). |
| P-FMV/EF-1α | 3100-4139 | Chimeric promoter consisting of enhancer sequences from the promoter of the Figwort Mosaic virus (FMV) 35S RNA (Richins et al., Nucleic Acids Research 15: 8451-8466, 1987) combined with the promoter from the EF-1αgene of *Arabidopsis thaliana* that encodes elongation factor EF-1 alpha (Axelos et al., Molecular and General Genetics 219: 106-112, 1989). It is associated with constitutive expression of the gene. |
| $L^5$-EF-1α | 4140-4185 | Leader (exon 1) of the EF-1αgene from *Arabidopsis thaliana* that encodes elongation factor EF-1 alpha (Axelos et al., Molecular and General Genetics 219: 106-112, 1989), which enhances gene expression. |
| $I^6$-EF-1α | 4186-4807 | Intron with flanking splice sites of the EF-1α gene from *Arabidopsis thaliana* that encodes elongation factor EF-1 alpha (Axelos et al., Molecular and General Genetics 219: 106-112, 1989), that enhances gene expression. |
| $TS^7$-CTP2 | 4817-5044 | Targeting sequence of the ShkG gene from *Arabidopsis thaliana* encoding EPSPS containing the transit peptide region) that directs transport of the EPSPS protein to the chloroplast (Klee et al., Molecular and General Genetics 210: 437-442, 1987). |
| CS-modified cp4 epsps | 5045-6412 | Codon modified coding sequence of the aroA gene from the *Agrobacterium* sp. strain CP4 encoding the CP4 EPSPS protein (Padgette et al., 1996, in Herbicide-Resistant Crops: Agricultural, Economic, Environmental, Regulatory, and Technological Aspects, S.O. Duke, (ed.), Pages 53-84, CRC Press, Boca Raton, FL). |
| T-E9 | 6419-7061 | 3' nontranslated region of the RbcS2 gene from *Pisum sativum* (pea) encoding the Rubisco small subunit, which functions to direct polyadenylation of the mRNA (Coruzzi et al., EMBO J. 3: 1671-1679, 1984). |
| B-Left Border | 7076-7486 | DNA region from *Agrobacterium tumefaciens* containing the left border sequence used for transfer of the T-DNA (Barker et al., Plant Mol. Biol. 2: 335-350, 1983). |

Vector Backbone

| Genetic Element | Location | Function (Reference) |
|---|---|---|
| aadA | 7582-8470 | Bacterial promoter, coding sequence, and 3' UTR for an aminoglycoside-modifying enzyme, 3"(9)-O-nucleotidyltransferase from the transposon Tn7 (Fling et al., Nucleic Acids Research 13: 7095-7106, 1985) that confers spectinomycin and streptomycin resistance. |
| $OR^8$-ori-pBR322 | 9001-9589 | Origin of replication from pBR322 for maintenance of plasmid in *E. coli* (Sutcliffe, 1979, Complete nucleotide sequence of the *Escherichia coli* plasmid pBR322. Pages 77-90 in Cold Spring Harbor Symposia on Quantitative Biology, Cold Spring Harbor, NY, Cold Spring Harbor Laboratory Press). |
| CS-rop | 10017-10208 | Coding sequence for repressor of primer protein derived from the ColE1 plasmid for maintenance of plasmid copy number in *E. coli* (Giza and Huang, Gene 78: 73-84, 1989). |

TABLE 1-continued

Summary of the genetic elements in pMON83132.

| Genetic Element | Location in Construct pMON83132 | Function (Reference) |
|---|---|---|
| OR-ori V | 10946-11342 | Origin of replication from the broad host range plasmid RK2 for maintenance of plasmid in *Agrobacterium* (Stalker et al., Molecular and General Genetics 181: 8-12, 1981). |

[1]B, Border
[2]P, Promoter
[3]CS, Coding Sequence
[4]T, Transcription Termination Sequence
[5]L, Leader
[6]I, Intron
[7]TS, Targeting Sequence
[8]OR, Origin of Replication At the R1 generation, events underwent segregation analysis to select only homozygous and heterozygous plants going forward. In addition, CP4 linkage analysis, TAQ-MAN® analysis and BBX32 expression analysis were performed to remove events where CP4 was linked to the BBX32 transgene, or where the sequence of the OriV origin of replication (backbone) was detected, or where BBX32 transgene expression level was undesirable, resulting in 121 events remaining. Southern hybridization analysis using different probes further eliminated 42 events that were not single copy, or single insert or not backbone-free. Probes included the intact BBX32 coding region and its respective promoter, the polyadenylation sequence and the plasmid backbone. An additional 2 events were stopped due to lack of sufficient seeds to advance, leaving 77 events to carry forward to the R2 generation.

Figure 2:
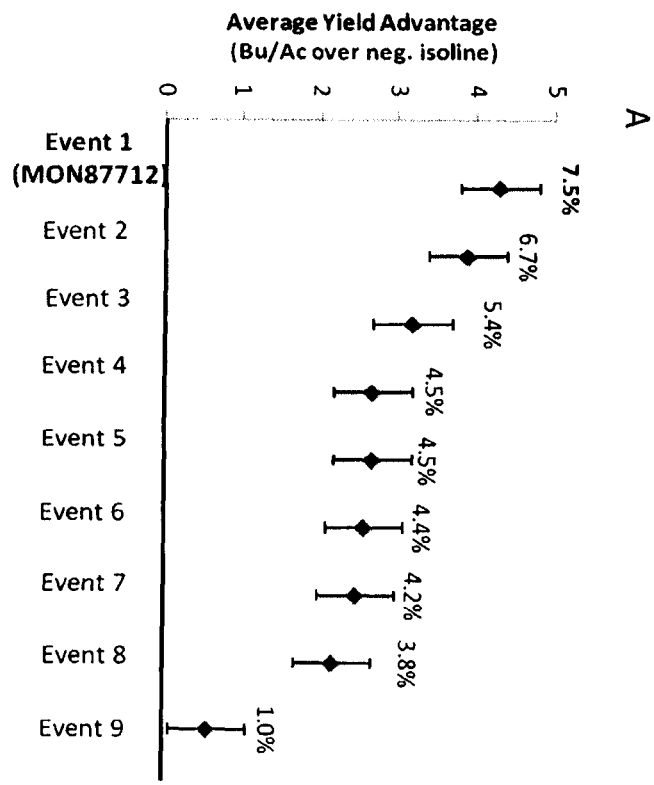
FIG. 2. Meta-analysis of yield data for 9 transgenic events from 4 field seasons of field testing in the United States or South America, showing event 1 comprising MON87712 DNA with the highest yield. Panel A: average yield increases of transgenic events over their corresponding negative isolines (bushel/acre). Panel B: average yield increases of transgenic events over wild type control (bushel/acre). The numbers above each bar represent % increase.
Figure 2:
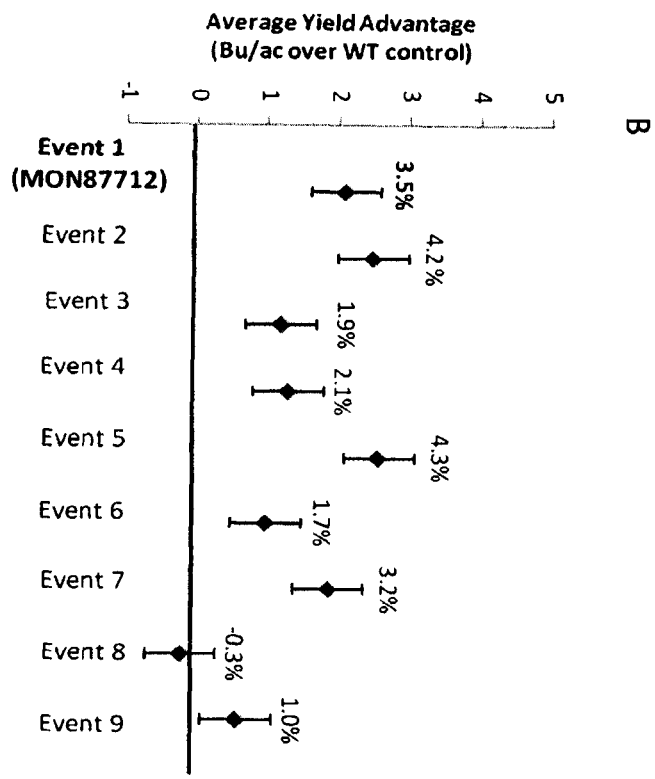

At the R2 generation, an additional 9 events were dropped due to 1) lack of sufficient seed for the R2 nursery (1 event), or 2) undesirable agronomic phenotypes (2 events), or 3) BBX32 expression level or the absence of the representative homozygous lines as determined by Invader[R] (Third Wave Technologies, Inc., Madison, Wis.) (6 events). As a result, 68 events were carried forward for year 1 yield field test in the US. Based upon yield performance, 16 events were advanced to the second season field testing in South America, from which, 9 events were selected for further yield testing. Meta-analysis of yield data from 4 seasons of field trials in the United States or South America, each with multiple locations (Table 2), showed that one progeny line designated as comprising event MON87712 was the highest yielding event (FIG. 2).

TABLE 2

Details of the four season field testing for yield.

| Year | Geography | # Locations |
|---|---|---|
| 2007 | United States | 18 |
| 2007-2008 | South America | 14 |
| 2008 | United States | 24 |
| 2008-2009 | South America | 14 |

Example 2: Isolation of Flanking Sequences Using Inverse PCR and Identification of Flanking Sequences by Sequencing This example describes isolation of the soybean genomic DNA sequences flanking the transgenic DNA insert using inverse PCR for event MON87712, and identification of the flanking genomic sequences by sequencing.

Sequences flanking the T-DNA insertion in event MON87712 were determined using inverse PCR as described in Ochman et al., 1990 (PCR Protocols: A guide to Methods and Applications, Academic Press, Inc.). Plant genomic DNA was isolated from both wild-type A3525 and the transgenic line from tissue grown under greenhouse conditions. Frozen leaf tissue was ground with a mortar and a pestle in liquid nitrogen or by mechanical grinding, followed by DNA extraction using methods known in the art. This method can be modified by one skilled in the art to extract DNA from any tissue, including, but not limited to seed.

An aliquot of DNA from each sample was digested with restriction endonucleases selected based on restriction analysis of the transgenic DNA. After self-ligation of the restriction fragments, PCR amplification was performed using primers designed from the transgenic sequence that would amplify sequences extending away from the 5' and 3' ends of the transgenic DNA. A variety of Taq polymerases and amplification systems may be used. Table 3 shows an example of PCR amplification for flanking sequence isolation using Phusion High Fidelity DNA Polymerase (Cat. No. F531S or F531L, New England Biolabs), and Thermalcyclers Applied Biosystems GeneAmp 9700, ABI 9800 Fast Thermal Cycler and MJ Opticon.

TABLE 3

An example of inverse PCR amplification for flanking sequence isolation.

| | Volume | Component |
|---|---|---|
| PCR master mix (per reaction) | 2.9 µl | Water |
| | 0.05 µl | Primer 1 (100 µM) |
| | 0.05 µl | Primer 1 (100 µM) |
| | 5.0 µl | 2X Phusion Taq |
| | 2.0 µl | ligated DNA |
| | 10 µl | Total |

| | Step | Condition |
|---|---|---|
| DNA amplification in a fast thermocycler | 1 | 98° C. 30 sec |
| | 2 | 98° C. 5 sec |
| | 3 | 60° C. 10 sec |
| | 4 | 72° C. 2 min |

TABLE 3-continued

An example of inverse PCR amplification
for flanking sequence isolation.

| 5 | Go to step 2 30 times |
| 6 | 72° C. 4 min |
| 7 | 10° C. forever |
| 8 | End |

PCR products were separated by agarose gel electrophoresis and purified using a QIAGEN gel purification kit (Qiagen, Valencia, Calif.). The subsequent products were sequenced directly using standard sequencing protocols. Using these two methods, the 5' flanking sequence, which extends into the left border sequence of the integrated DNA insert including the BBX32 expression cassette, was identified and is presented as SEQ ID NO: 3 ([C] of FIG. 1). The 3' flanking sequence, which extends into the right border sequence of the integrated DNA insert including the BBX32 expression cassette, was identified and is presented as SEQ ID NO: 4 ([D] of FIG. 1). The transgenic DNA integrated into the soybean genomic DNA is presented as SEQ ID NO: 5 ([E] of FIG. 1).

The isolated sequences were compared to the T-DNA sequence to identify the flanking sequences and the co-isolated T-DNA fragments. Confirmation of the presence of the expression cassette was achieved by PCR with primers designed based upon the deduced flanking sequence data and the known T-DNA sequence. The wild type sequence corresponding to the same region in which the T-DNA was integrated in the transformed line was isolated using primers designed from the flanking sequences in MON87712. The flanking sequences in MON87712 and the wild type sequence were analyzed against multiple nucleotide and protein databases. This information was used to examine the relationship of the transgene to the plant genome and to look at the insertion site integrity. The flanking sequence and wild type sequences were used to design primers for TAQMAN® endpoint assays used to identify the events and determine zygosity as described in Example 3.

Example 3: Event-Specific Endpoint TAQMAN® and Zygosity Assays

This example describes an event-specific endpoint TAQ-MAN® thermal amplification method for identification of event MON87712 DNA in a sample.

Examples of conditions useful with the event MON87712-specific endpoint TAQMAN® method are described in Table 4 and Table 5. The DNA primers used in the endpoint assay are primers SQ3983 (SEQ ID NO: 16) and SQ22982 (SEQ ID NO: 17) and the 6-FAM™ labeled oligonucleotide probe is PB10453 (SEQ ID NO: 18). 6FAM™ is a fluorescent dye product of Applied Biosystems (Foster City, Calif.) attached to the DNA probe. For TAQ-MAN® MGB (Minor Groove Binding) probes, the 5'exonuclease activity of Taq DNA polymerase cleaves the probe from the 5'-end, between the fluorophore and quencher. When hybridized to the target DNA strand, quencher and fluorophore are separated enough to produce a fluorescent signal.

Primers SQ3983 (SEQ ID NO: 16) and SQ22982 (SEQ ID NO: 17), when used as described with probe PB10453 (SEQ ID NO: 18), produce an amplicon that is diagnostic for event MON87712 DNA. The analysis includes a positive control from soybean known to contain event MON87712 DNA, a negative control from non-transgenic soybean and a negative control that contains no template DNA.

These assays are optimized for use with Applied Biosystems GeneAmp PCR System 9700, ABI 9800 Fast Thermal Cycler and MJ Opticon. Other methods and apparatus known to those skilled in the art may be used to produce amplicons that identify the event MON87712 DNA.

TABLE 4

Soybean MON87712 Event-Specific Endpoint
TAQMAN® PCR Conditions

| Step | Reagent | Volume | Comments |
|---|---|---|---|
| 1 | 18 megohm water | adjust for final volume of 10 µl | |
| 2 | 2X Universal Master Mix (dNTPs, enzyme and buffer) | 5.0 µl | 1X final concentration of dNTPs, enzyme and buffer |
| 3 | Event Primers SQ3983 and SQ22982 Mix (resuspended in 18 megohm water to a concentration of 20 µM for each primer) Example: In a microcentrifuge tube, the following are added to achieve 500 µl at a final concentration of 20 µM: 100 µl of Primer SQ22982 at a concentration of 100 µM 100 µl of Primer SQ3983 at a concentration of 100 µM 300 µl of 18 megohm water | 0.5 µl | 1.0 µM final concentration |
| 4 | Event 6-FAM™ MGB Probe PB10453 (resuspended in 18 megohm water to a concentration of 10 µM) | 0.2 µl | 0.2 µM final concentration |
| 5 | Internal control Primer-1 and internal control Primer-2 Mix (resuspended in 18 megohm water to a concentration of 20 µM for each primer) | 0.5 µl | 1 µM final concentration |
| 6 | Internal control VIC™ probe (resuspended in 18 megohm water to a concentration of 10 µM) | 0.2 µl | 0.2 µM final concentration |
| 7 | Extracted DNA (template): 1. Leaf or seed samples to be analyzed 2. Negative control (non-transgenic DNA) 3. Negative water control (no template control) 4. Positive control (MON87712 DNA) | 3.0 µl | |

TABLE 5

Endpoint TAQMAN® thermocycler conditions

| Cycle No. | Settings | |
|---|---|---|
| 1 | 50° C. | 2 minutes |
| 1 | 95° C. | 10 minutes |
| 10 | 95° C. | 15 seconds |
| | 64° C. | 1 minute (−1° C./cycle) |
| 30 | 95° C. | 15 seconds |
| | 54° C. | 1 minute |
| 1 | 10° C. | Forever |

The following example describes an event-specific endpoint TAQMAN® thermal amplification method developed to determine the zygosity of event MON87712 in a sample.

A zygosity assay is useful for determining if a plant comprising an event is homozygous for the event DNA, that is comprising the exogenous DNA at the same location on each chromosome of a chromosomal pair; or heterozygous for an event DNA, that is comprising the exogenous DNA on only one chromosome of a chromosomal pair; or is null for the event DNA, that is wild type. A set of three primers (SEQ ID NO: 10, 13 and 11 or 15), a 6FAM™ labeled probe (SEQ ID NO: 12) and a VIC™ labeled probe (SEQ ID NO: 14) were used in the assays (Table 8). 6FAM™ and VIC™ are fluorescent dye products of Applied Biosystems (Foster City, Calif.) attached to the DNA probes. Primer SEQ ID NO: 11 or 15 hybridizes and extends specifically from the inserted exogenous DNA; primer SEQ ID NO: 10 hybridizes and extends specifically from the DNA flanking the 3' side of the inserted exogenous DNA; primer SEQ ID NO: 13 hybridizes and extends specifically from the wild-type DNA corresponding to a region that was deleted during T-DNA insertion in the transgenic event MON87712. These primers are diagnostic. In this example, primers SEQ ID NO: 10 and SEQ ID NO: 11 or 15 and the 6FAM™-labeled oligonucleotide probe SEQ ID NO: 12 produce a DNA amplicon revealed by the liberation of a fluorescent signal from probe SEQ ID NO: 12, which is diagnostic for event MON87712 DNA, indicating a copy of the inserted transgenic DNA present in the genomic DNA. Primers SEQ ID NO: 10 and SEQ ID NO: 13 and the VIC™-labeled oligonucleotide probe SEQ ID NO: 14 produce an amplicon revealed by the liberation of a fluorescent signal from probe SEQ ID NO: 14, which is diagnostic for the wild type allele, indicating no copy of the inserted exogenous DNA present in the genomic DNA. When the three primers and two probes are mixed together in a PCR reaction with DNA extracted from a plant, release of a fluorescent signal only from the 6FAM™-labeled oligonucleotide probe (SEQ ID NO: 12) is indicative of and diagnostic of a plant homozygous for event MON87712. When the three primers and two probes are mixed together in a PCR reaction with DNA extracted from a plant, release of a fluorescent signal from both the 6FAM™-labeled oligonucleotide probe SEQ ID NO: 12 and the VIC™-labeled oligonucleotide probe SEQ ID NO: 14 is indicative of and diagnostic of a plant heterozygous for event MON87712. When the three primers and two probes are mixed together in a PCR reaction with DNA extracted from a plant, release of a fluorescent signal from only the VIC™-labeled oligonucleotide probe SEQ ID NO: 14 is indicative of and diagnostic of a plant null for event MON87712, i.e. wild type. The assays also include a positive control from soybean containing event MON87712 DNA, a negative control from non-transgenic soybean and a negative control that contains no template DNA.

Table 6 and Table 7 provide examples of conditions used for zygosity assay for event MON87712 in a sample. These assays are optimized for use with an Applied Biosystems GeneAmp PCR System 9700. The allelic detection was optimized with a 7900HT Sequence Detection System by Applied Biosytems, or a PHERAstar by BMG Labtech. Other methods and apparatus known to those skilled in the art that produce amplicons that identify the event MON87712 DNA is within the skill of the art.

TABLE 6

Soybean MON87712 Event-Specific Zygosity Endpoint TAQMAN ® PCR

| Step | Details | |
|---|---|---|
| 1 | Prepare the following:<br>200 µM Primers<br>100 µM Event 6-FAM ™ MGB* probe<br>100 µM Wild type VIC ™ MGB probe<br>50:50 2X ABI universal master mix: 2X AbGene universal master mix 0.1X TE | |
| 2 | Prepare the following 80X Primer + probe stock: | |
| | 100 µM Event 6-FAM ™ MGB Probe | 16 µl |
| | 100 µM Wild type VIC ™ MGB probe | 16 µl |
| | 200 µM Wild type forward primer | 8.5 µl |
| | 200 µM Event forward primer | 8.5 µl |
| | 200 µM reverse primer | 17 µl |
| 3 | Dilute the 80X Primer + Probe stock to 10X working dilution with 0.1X TE | |
| 4 | Prepare the following reaction solution (per reaction): | |
| | 50:50 2X ABI universal master mix: | |
| | 2X AbGene universal master mix | 3 µl |
| | 10X Primer + Probe working dilution | 0.6 µl |
| | Extracted DNA (template): | 2.4 µl |
| | 1) Samples to be analyzed | |
| | 2) Negative control (non-transgenic DNA) | |
| | 3) Negative water control (no template control) | |
| | 4) Positive control homozygous MON87712 DNA | |
| | 5) Positive control heterozygous MON87712 DNA | |

*MGB: Minor Groove Binding

TABLE 7

Zygosity Endpoint TAQMAN ® Thermocycler Conditions

| Cycle No. | Settings | |
|---|---|---|
| 1 | 95° C. | 10 minutes |
| 40 | 92° C. | 15 seconds |
| | 64° C. | 1 Minute |
| 1 | 10° C. | Forever |

TABLE 8

Examples of Primer And Probe Combinations Used for Zygosity Assays

| Combination | Type | Direction | SEQ ID NO | Sequences |
|---|---|---|---|---|
| 1 | Primers | Reverse | 10 | GTTTTACAATTACCTCGTTTAAGTAAATCA |
|  |  | Forward | 13 | CTATTATTTGCTATAAGTATTTGATGTAAGAA |
|  | Probe | Wild type allele | 14 | VIC-TTGTATTAATAACAAAAAATTG |
|  | Primers | Reverse | 10 | GTTTTACAATTACCTCGTTTAAGTAAATCA |
|  |  | Forward | 11 | CATTCTCGAGCAGGACCTGCAGAA |
|  | Probe | MON87712 allele | 12 | 6FAM-AACACTGATAGTTTAAACTGAAG |
| 2 | Primers | Reverse | 10 | GTTTTACAATTACCTCGTTTAAGTAAATCA |
|  |  | Forward | 13 | CTATTATTTGCTATAAGTATTTGATGTAAGAA |
|  | Probe | Wild type allele | 14 | VIC-TTGTATTAATAACAAAAAATTG |
|  | Primers | Reverse | 10 | GTTTTACAATTACCTCGTTTAAGTAAATCA |
|  |  | Forward | 15 | GTACATTCTCGAGCAGGACCTGCA |
|  | Probe | MON87712 allele | 12 | 6FAM-AACACTGATAGTTTAAACTGAAG |

Example 4: Identification of Event MON87712 in any MON87712 Containing Breeding Event This example describes how one may identify the MON87712 event within progeny of any breeding event containing MON87712 soybean.

Event DNA primer pairs are used to produce an amplicon diagnostic for soybean event MON87712. An amplicon diagnostic for MON87712 comprises at least one junction sequence, provided herein as SEQ ID NO: 1, SEQ ID NO: 2, at least 51 consecutive nucleotides of SEQ ID NO: 7, or at least 51 consecutive nucleotides of SEQ ID NO: 8, or the complements thereof ([A] or [B], respectively as illustrated in FIG. 1). SEQ ID NO: 1 ([A] of FIG. 1) is a nucleotide sequence corresponding to the junction of the 5' flanking sequence (positions 3495 through 3516 of SEQ ID NO: 3 [C], see FIG. 1) and the left border of the integrated DNA insert (positions 1 through 11 of SEQ ID NO: 5 [E], see FIG. 1). SEQ ID NO: 2 ([B] of FIG. 1) is a nucleotide sequence corresponding to the junction of the right border of the integrated DNA insert (positions 2004 through 2014 of SEQ ID NO: 5 [E], see FIG. 1) and the 3' flanking sequence (positions 90 through 111 of SEQ ID NO: 4 [D], see FIG. 1). SEQ ID NO: 7 ([A] of FIG. 1) is a nucleotide sequence corresponding to the junction of the 5' flanking sequence (positions 3456 through 3555 of SEQ ID NO: 3 [C], see FIG. 1) and the left border of the integrated DNA insert (positions 1 through 50 of SEQ ID NO: 5 [E], see FIG. 1). SEQ ID NO: 8 ([B] of FIG. 1) is a nucleotide sequence corresponding to the junction of the right border of the integrated DNA insert (positions 1965 through 2014 of SEQ ID NO: 5 [E], see FIG. 1) and the 3' flanking sequence (positions 51 through 150 of SEQ ID NO: 4 [D], see FIG. 1).

Event primer pairs that produce an amplicon diagnostic for MON87712 include primer pairs designed using the flanking sequences (SEQ ID NO: 3 and SEQ ID NO: 4) and the integrated transgenic DNA sequence (SEQ ID NO: 5). To acquire a diagnostic amplicon in which at least 15 nucleotides of SEQ ID NO: 1 is found, one would design a forward primer based upon SEQ ID NO: 3 from bases 1 through 3494 and a reverse primer based upon the inserted expression cassette DNA sequence, SEQ ID NO: 5 from positions 12 through 2014, in which the primers are of sufficient length of contiguous nucleotides to specifically hybridize to SEQ ID NO: 3 and SEQ ID NO: 5. To acquire a diagnostic amplicon in which at least 15 nucleotides of SEQ ID NO: 2 is found, one would design a forward primer based upon the inserted expression cassette DNA sequence, SEQ ID NO: 5, from positions 1 through 2003 and a reverse primer based upon the 3' flanking sequence, SEQ ID NO: 4, from bases 12 through 2065, in which the primers are of sufficient length of contiguous nucleotides to specifically hybridize to SEQ ID NO: 4 and SEQ ID NO: 5. For practical purposes, one should design primers that produce amplicons of a limited size range, for example, between 100 to 1000 bases. Smaller sized (shorter nucleotide length) amplicons in general may be more reliably produced in PCR reactions, allow for shorter cycle times and be easily separated and visualized on agarose gels or adapted for use in endpoint TAQMAN®-like assays. In addition, amplicons produced using primer pairs can be cloned into vectors, propagated, isolated and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for MON87712, plants comprising MON87712 or progeny thereof is an aspect of the present invention. Any single isolated DNA primer molecule comprising at least 11 contiguous nucleotides of SEQ ID NO: 3, or its complement that is useful in a DNA amplification method to produce an amplicon diagnostic for MON87712, plants comprising MON87712 or progeny thereof is an aspect of the present invention. Any single isolated DNA primer molecule comprising at least 11 contiguous nucleotides of SEQ ID NO: 4, or its complement that is useful in a DNA amplification method to produce an amplicon diagnostic for MON87712, plants comprising MON87712 or progeny thereof is an aspect of the present invention. Any single isolated DNA primer molecule comprising at least 11 contiguous nucleotides of SEQ ID NO: 5, or its complement that is useful in a DNA amplification method to produce an amplicon diagnostic for MON87712, plants comprising MON87712 or progeny thereof is an aspect of the present invention.

An example of the amplification conditions for this analysis is illustrated in Table 4 and Table 5 (Example 3). However, any modification of these methods or the use of DNA primers homologous or complementary to SEQ ID NO: 3, SEQ ID NO: 4 or DNA sequences of the transgenic insert (SEQ ID NO: 5) of event MON87712 that produce an amplicon diagnostic for MON87712 is within the scope of the present disclosure. A diagnostic amplicon comprises a DNA molecule homologous or complementary to at least one transgene/genomic junction DNA (SEQ ID NO: 1, SEQ ID NO: 2, at least 51 consecutive nucleotides of SEQ ID NO: 7, or at least 51 consecutive nucleotides of SEQ ID NO: 8, or the complements thereof), or a substantial portion thereof.

An analysis for event MON87712 DNA in a sample should include a positive control from event MON87712, a negative control from a soybean plant that does not contain event MON87712, for example, but not limited to wild type control, and a negative control that contains no soybean genomic DNA. A primer pair that will amplify an endogenous soybean DNA molecule will serve as an internal control for the DNA amplification conditions. Additional primer sequences can be selected from SEQ ID NO: 3, SEQ ID NO: 4, or SEQ ID NO: 5 by those skilled in the art of DNA amplification methods, and conditions selected for the production of an amplicon by the methods shown in Table 4 and Table 5 may differ, but result in an amplicon diagnostic for event MON87712 DNA. The use of these DNA primer sequences with modifications to the methods of Table 4 and Table 5 are within the scope of the invention. The amplicon produced by at least one DNA primer sequence derived from SEQ ID NO: 3, SEQ ID NO: 4, or SEQ ID NO: 5 that is diagnostic for MON87712 is an aspect of the invention.

DNA detection kits that contain at least one DNA primer derived from SEQ ID NO: 3, SEQ ID NO: 4, or SEQ ID NO: 5, that when used in a DNA amplification method, produces a diagnostic amplicon for MON87712, plants comprising MON87712 or progeny thereof is an aspect of the invention. A soybean plant or seed, wherein its genomic DNA produces an amplicon diagnostic for MON87712 when tested in a DNA amplification method is an aspect of the invention. The assay for the MON87712 amplicon can be performed by using an Applied Biosytems GeneAmp PCR System 9700, ABI 9800 Fast Thermal Cycler and MJ Opticon, Stratagene Robocycler, MJ Engine, Perkin-Elmer 9700 or Eppendorf Mastercycler Gradient thermocycler or any other amplification system that can be used to produce an amplicon diagnostic of MON87712.

A deposit of the soybean event MON87712 comprising seed disclosed above and recited in the claims, has been made under the Budapest Treaty with the American Type Culture Collection (ATCC), 10801 University Boulevard, Manassas, Va. 20110. The date of deposit is Aug. 20, 2009 and the ATCC accession number is PTA-10296. Upon issuance of a patent, all restrictions upon the deposit will be removed, and the deposit is intended to meet all of the requirements of 37 C.F.R. §§ 1.801-1.809. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

The invention claimed is:

1. A polynucleotide probe diagnostic for the presence of event MON87712 DNA, wherein said polynucleotide probe is of sufficient length to bind to a nucleic acid molecule comprising SEQ ID NO: 1, SEQ ID NO: 2, or at least 55 consecutive nucleotides of SEQ ID NO: 7 or of SEQ ID NO: 8, or full-length complements thereof, and wherein said polynucleotide probe hybridizes under stringent hybridization conditions with a DNA molecule comprising SEQ ID NO: 1, SEQ ID NO: 2, or at least 55 consecutive nucleotides of SEQ ID NO: 7 or of SEQ ID NO: 8, or full-length complements thereof and does not hybridize under stringent hybridization conditions with a DNA molecule not comprising SEQ ID NO: 1, SEQ ID NO: 2, or at least 55 consecutive nucleotides of SEQ ID NO: 7 or of SEQ ID NO: 8, or full-length complements thereof.

2. A method of detecting the presence of a DNA molecule derived from event MON87712 in a DNA sample, the method comprising:
   a) contacting said DNA sample with the polynucleotide probe of claim 1;
   b) subjecting said DNA sample and said polynucleotide probe to stringent hybridization conditions; and
   c) detecting hybridization of said polynucleotide probe to said DNA molecule derived from event MON87712 in said DNA sample.

3. A pair of DNA molecules comprising a first DNA molecule and a second DNA molecule different from the first DNA molecule, capable of functioning as DNA primers when used together in an amplification reaction with a template derived from event MON87712 to produce an amplicon diagnostic for event MON87712 DNA in a sample, wherein said amplicon comprises a nucleotide sequence comprising SEQ ID NO: 1, SEQ ID NO: 2, or 55 consecutive nucleotides of SEQ ID NO: 7, or of SEQ ID NO: 8, or full-length complements thereof.

4. A method of detecting the presence of a DNA molecule derived from event MON87712 in a DNA sample, said method comprising:
   a) contacting said DNA sample with said pair of DNA molecules of claim 3;
   b) performing an amplification reaction to produce an amplicon comprising a nucleotide sequence comprising SEQ ID NO: 1, SEQ ID NO: 2, or 55 consecutive nucleotides of SEQ ID NO: 7, or of SEQ ID NO: 8, or full-length complements thereof; and
   c) detecting said amplicon.

5. A DNA detection kit comprising:
   a) a polynucleotide probe diagnostic for the presence of event MON87712 DNA, wherein said polynucleotide probe is of sufficient length to bind to a nucleic acid molecule comprising SEQ ID NO: 1, SEQ ID NO: 2, or at least 55 consecutive nucleotides of SEQ ID NO: 7 or of SEQ ID NO: 8, or full-length complements thereof, and wherein said polynucleotide probe hybridizes under stringent hybridization conditions with a DNA molecule comprising SEQ ID NO: 1, SEQ ID NO: 2, or at least 55 consecutive nucleotides of SEQ ID NO: 7 or of SEQ ID NO: 8, or full-length complements thereof and does not hybridize under stringent hybridization conditions with a DNA molecule not comprising SEQ ID NO: 1, SEQ ID NO: 2, or at least 55 consecutive nucleotides of SEQ ID NO: 7 or of SEQ ID NO: 8, or full-length complements thereof; or
   b) a pair of DNA molecules comprising a first DNA molecule and a second DNA molecule different from the first DNA molecule, capable of functioning as DNA primers when used together in an amplification reaction with a template derived from event MON87712 to produce an amplicon diagnostic for event MON87712 DNA in a sample, wherein said amplicon comprises a nucleotide sequence comprising SEQ ID NO: 1, SEQ ID NO: 2, or 55 consecutive nucleotides of SEQ ID NO: 7, or of SEQ ID NO: 8, or full-length complements thereof.

6. The DNA detection kit of claim 5, wherein the polynucleotide probe comprises SEQ ID NO: 1, SEQ ID NO: 2, or 55 consecutive nucleotides of SEQ ID NO: 7, or SEQ ID NO: 8 or full-length complements thereof.

* * * * *